US007270830B2

(12) United States Patent
Reidenberg et al.

(10) Patent No.: US 7,270,830 B2
(45) Date of Patent: Sep. 18, 2007

(54) TRANSDERMAL BUPRENORPHINE DOSAGE REGIMEN FOR ANALGESIA

(75) Inventors: Bruce E. Reidenberg, Rye, NY (US); Daniel A. Spyker, Burlingame, CA (US)

(73) Assignee: Purdue Pharma L.P., Stamford, CT (US)

( * ) Notice: Subject to any disclaimer, the term of this patent is extended or adjusted under 35 U.S.C. 154(b) by 678 days.

(21) Appl. No.: 10/736,043

(22) Filed: Dec. 15, 2003

(65) Prior Publication Data

US 2004/0126416 A1 Jul. 1, 2004

Related U.S. Application Data

(60) Provisional application No. 60/433,423, filed on Dec. 13, 2002.

(51) Int. Cl.
*A61F 13/00* (2006.01)

(52) U.S. Cl. .................................................... 424/449

(58) Field of Classification Search ................ 424/443, 424/449, 489, 490; 514/282

See application file for complete search history.

(56) References Cited

U.S. PATENT DOCUMENTS

| | | | |
|---|---|---|---|
| 4,806,341 | A | 2/1989 | Chien et al. |
| 5,026,556 | A | 6/1991 | Drust et al. |
| 5,069,909 | A | 12/1991 | Sharma et al. |
| 5,149,538 | A | 9/1992 | Granger et al. |
| 5,225,199 | A | 7/1993 | Hidaka et al. |
| 5,240,711 | A | 8/1993 | Hille et al. |
| 5,613,958 | A | 3/1997 | Kochinke et al. |
| 5,968,547 | A | 10/1999 | Reder et al. |
| 2001/0002259 | A1 | 5/2001 | Reder et al. |

FOREIGN PATENT DOCUMENTS

| | | |
|---|---|---|
| WO | WO-03/079945 | 10/2003 |
| WO | WO-2004/103317 | 12/2004 |
| WO | WO-2005/011579 | 2/2005 |

OTHER PUBLICATIONS

Adrianensen et al., Acta Anaesthesiol Belg 1985;36:33-40.
Brema et al., Int J Clin Pharmacol Res 1996;16:109-116.
Capogna et al., Anaesthesia 1988, 43:128-130.
Goodman & Gilman's The Pharmacological Basis of Therapeutics, J.G. Hardman (Ed.), McGraw-Hill Professional Publishing 2001, pp. 530-532.
Hale et al., Abstract, 08 GSA 2001.
Hale et al., Abstract, Nat'l Clin. Symposium of the American College of Nurse Practitioners; Oct. 2001.
Hale et al., J. Clin. Pharmacol. 2001; 41(9):1027, Abstract 58.
Heel et al., Drugs 1979;17:81-110.
Inagaki et al., Anesth Analg 1996;83:530-536.
Nasar et al., Curr Med Res Opin 1986;10:251-255.
Oda et al., Br. J. Anaesthesia 1999;82(6):900-903.
Reidenberg et al., J. Clin. Pharmacol. 2001;41(9):1027, Abstract 57.
Spyker et al., J. Amer. Geriatrics Soc. 2002;50(4):S66, Abstract P162.
Spyker et al., J. Pain 2002;3(2, Suppl. 1):12, Abstract 645.
Spyker et al., J. Pain 2002;3(2,Suppl 1):14, Abstract 653.
Spyker et al., Clin. Pharmacol. Ther. 2000;67(2):145, Abstract PIII-12.
Spyker et al., Clin. Pharmacol. Ther. 2001;69(2):P33, Abstract PII-3.
Spyker et al., Conference Abstract presented on Oct. 15, 2001.
Tauzin-Fin et al., Eur J Anaesthesiol 1998;15:147-152.
Ahmedzai, Eur. J. Cancer 1997;33:58-514.
Bentley et al., Anesth Anal 1982;61:968-971.
Cathelin et al., Anesth Anal (Paris). 1980;37(5-6):283-93.
Dayer et al., Drugs 1997;53:18-24.
Holdsworth et al., Gerontology 1994;40:32-37.
Jeal and Benfield, Drugs 1997;53:109-138.
Melon et al., Anesth Anal Rean 1980;37:121-125.
Mercandente, Cancer 1999;86:1856-66.
Mercadente and Fulfaro, Oncology 1999;13:215-220, 225.
Thompson et al., Br J Anaesth 1998;81:152-154.
Reidenberg et al., "Physiologic Effects of Buprenorphine Transdermal System (BTDS) Dose Escalation in the Young, Healthy Elderly and elderly Hypertensive Subjects," BIOSIS, Mar. 7, 2001; XP002389136; Meeting Abstract.

*Primary Examiner*—Sharon E. Kennedy
(74) *Attorney, Agent, or Firm*—Darby & Darby PC

(57) ABSTRACT

Dosage regimens of buprenorphine achieving rapid pain relief without increasing nausea, vomiting, or other adverse effects, are described. Also described are buprenorphine dosage regimens for treating chronic pain comprising administering to the patient (1) a first buprenorphine-containing transdermal dosage form for a first dosing period that is no more than about 5 days; (2) a second buprenorphine-containing transdermal dosage form for a second dosing period that is no more than 5 days, the second dosage form comprising the same dosage of buprenorphine as, or a greater dosage of buprenorphine than, the first dosage form; and (3) a third buprenorphine-containing transdermal dosage form for a third dosing period, the third dosage form comprising a greater dosage of buprenorphine than the second dosage form.

47 Claims, 11 Drawing Sheets

Vital Sign Assessments – BP, Pulse, Respiratory Rate, $SaO_2$

| | | | |
|---|---|---|---|
| 0, 1, 4, 8, 12, 24 h preapplication of BTDS 5 | Day 0 and 3 at 30 min, prior and 1, 2, 4, 8, 12, 20, 23, 36, 47, and 60 h post-application of BTDS 5 and BTDS 10 | Day 6 at 30 min, prior and 1, 2, 4, 8, 12, 20, 23, 36, 47, 60, 71, 84, 95, 108, 119, 132, 143, 156, and 164 h postapplication of BTDS 20 | Day 13 and at 0.25, 0.50, 0.75, 1, 2, 4, 8, 12, 24, 48, and 72 h postremoval of BTDS 20 |

| | | |
|---|---|---|
| 0, 23, and 47 h postapplication of BTDS 5 and BTDS 10 | 0, 23, 47, 71, 95, 119, and 143 h postapplication of BTDS 20 | 0.25, 0.50, 0.75, 1, 2, 4, 8, 12, 24, 48, and 72 h post-removal of BTDS 20 |

Pharmacokinetic Sampling

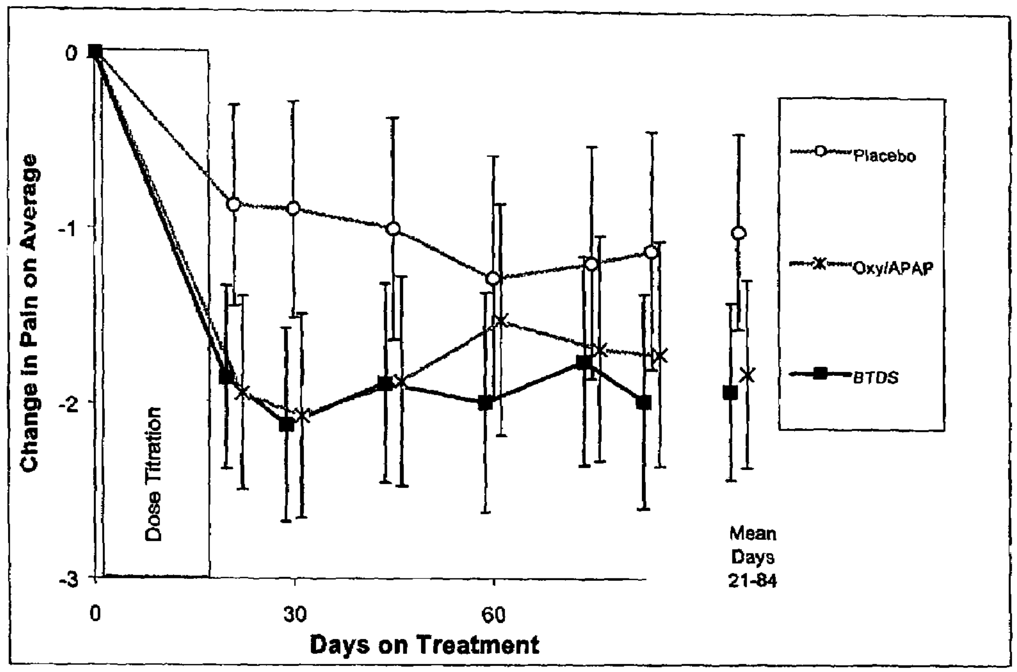

| | | Day 21 | Day 30 | Day 45 | Day 60 | Day 75 | Day 84 | RM 21-84 |
|---|---|---|---|---|---|---|---|---|
| **Placebo** | LS Mean ± SEM | -0.87 ± 0.38 | -0.89 ± 0.41 | -1.00 ± 0.42 | -1.26 ± 0.46 | -1.19 ± 0.44 | -1.12 ± 0.45 | -1.01 ± 0.37 |
| N=45 | N with data | 34 | 23 | 22 | 18 | 18 | 18 | 45 |
| **Oxy/APAP** | LS Mean ± SEM | **-1.94 ± 0.37** | **-2.07 ± 0.39** | -1.87 ± 0.40 | -1.52 ± 0.44 | -1.68 ± 0.43 | -1.71 ± 0.43 | -1.82 ± 0.36 |
| N= 42 | N with data | 31 | 32 | 29 | 29 | 28 | 27 | 42 |
| | Pairwise vs. Placebo | **P=0.015** | **P=0.013** | ns | ns | ns | ns | ns |
| **BTDS** | LS Mean ± SEM | **-1.85 ± 0.35** | **-2.12 ± 0.37** | -1.88 ± 0.38 | -1.99 ± 0.42 | -1.75 ± 0.40 | -1.98 ± 0.41 | **-1.92 ± 0.34** |
| N= 46 | N with data | 33 | 29 | 25 | 23 | 21 | 22 | 46 |
| | Pairwise vs. Placebo | **P=0.025** | **P=0.0093** | ns | ns | ns | ns | **P=0.035** |

*Least squares (LS) means - corrected by SAS Proc Mixed for baseline pain, center and opioid experience*
*Bar indicates time of dose titration: all BTDS patients started with BTDS 5 and titrated dose on Day 7 and/or Day 14*
*N = Number of patients with data at that visit; N for LOCF = N for the treatment group and was consistent over time*
*Bars at each data point indicate ± 1.5 SEM*
*RM 21-84 values calculated via repeated measures analysis of all available data from Days 21-84 using SAS Proc Mixed*
*Pairwise vs. Placebo - results of comparison with placebo using SAS Proc Mixed*
*ns = difference not statistically significant (P> 0.05)*
*Bolding indicates statistically significant reesults*

FIGURE 9

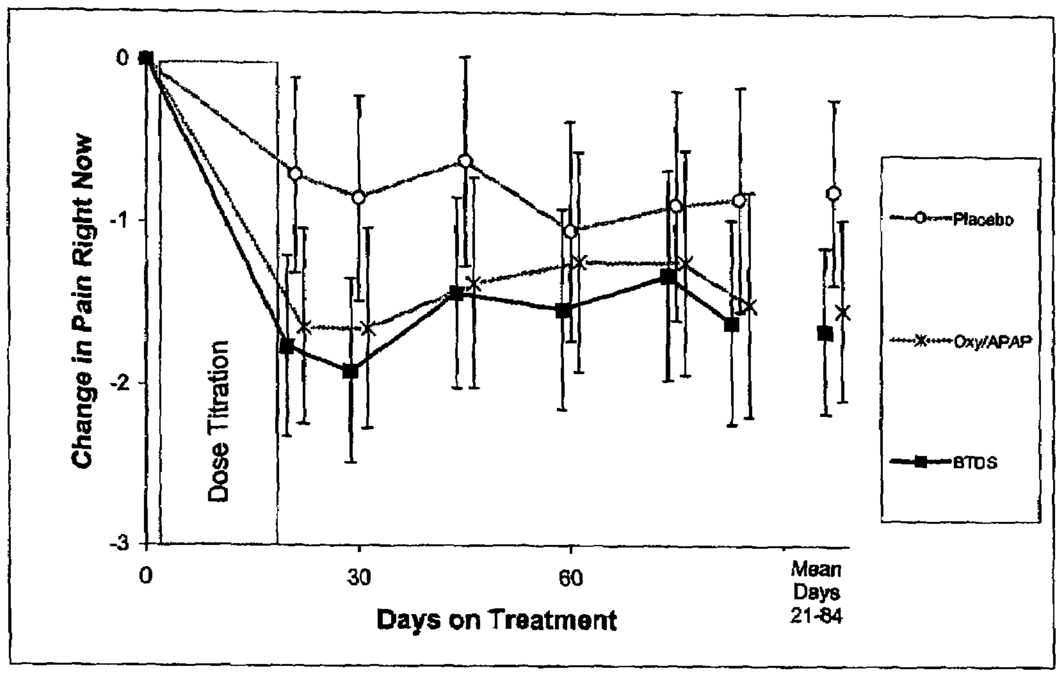

| | | Day 21 | Day 30 | Day 45 | Day 60 | Day 76 | Day 84 | RM 21-84 |
|---|---|---|---|---|---|---|---|---|
| Placebo | LS Mean ± SEM | -0.71 ± .040 | -0.85 ± 0.42 | -0.62 ± 0.43 | -1.05 ± 0.45 | -0.89 ± 0.47 | -0.85 ± 0.46 | -0.80 ± 0.38 |
| N=45 | N with data | 34 | 23 | 21 | 18 | 18 | 18 | 45 |
| Oxy/APAP | LS Mean ± SEM | **-1.64 ± 0.40** | -1.65 ± 0.41 | -1.37 ± 0.43 | -1.24 ± 0.45 | -1.24 ± 0.46 | -1.50 ± 0.46 | -1.53 ± 0.37 |
| N= 42 | N with data | **31** | 32 | 29 | 29 | 28 | 27 | 42 |
| | Pairwise vs. Placebo | ***P*=0.049** | ns | ns | ns | ns | ns | ns |
| BTDS | LS Mean ± SEM | **-1.76 ± 0.37** | **-1.91 ± 0.38** | -1.43 ± 0.39 | -1.53 ± 0.41 | -1.32 ± 0.43 | -1.61 ± 0.42 | **-1.66 ± 0.34** |
| N= 46 | N with data | **33** | **29** | 25 | 23 | 21 | 22 | **46** |
| | Pairwise vs. Placebo | ***P*=0.022** | ***P*=0.028** | *ns* | *ns* | *ns* | *ns* | ***P*=0.045** |

*Least squares (LS) means - corrected by SAS Proc Mixed for age category, baseline pain, center and opioid experience*
*Bar indicates time of dose titration: all BTDS patients started with BTDS 6 and titrated dose on Day 7 and/or Day 14*
*N = Number of patients with data at that visit; N for LOCF = N for the treatment group and was consistent over time*
*Bars at each data point indicate ± 1.5 SEM*
*RM 21-84 values calculated via repeated measures analysis of all available data from Days 21-84 using SAS Proc Mixed*
*Pairwise vs. Placebo - results of comparison with placebo using SAS Proc Mixed*
*ns = difference not statistically significant (P> 0.05)*
*Bolding indicates statistically significant results*

FIGURE 10

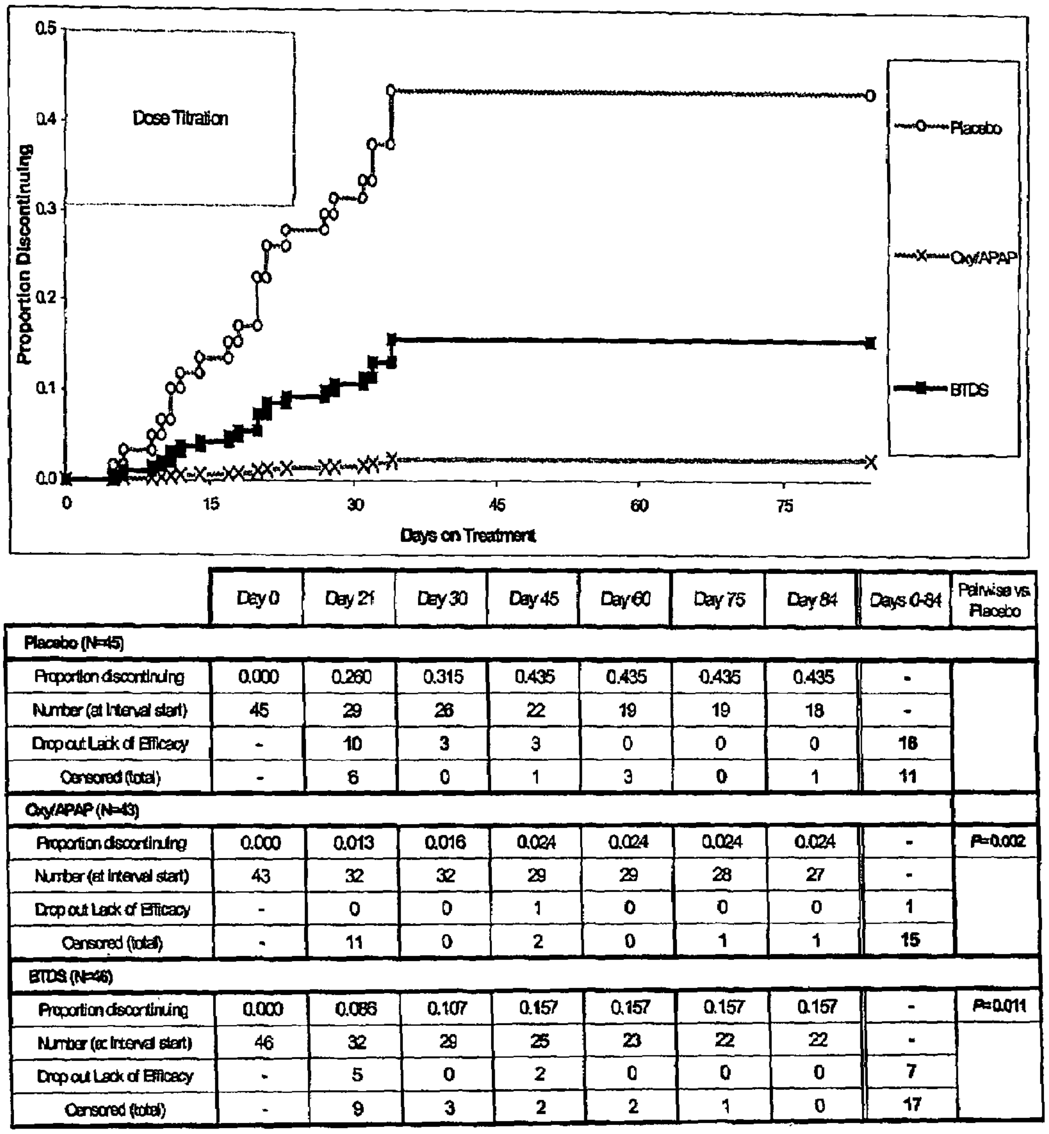

| | Day 0 | Day 21 | Day 30 | Day 45 | Day 60 | Day 75 | Day 84 | Days 0-84 | Pairwise vs. Placebo |
|---|---|---|---|---|---|---|---|---|---|
| **Placebo (N=45)** | | | | | | | | | |
| Proportion discontinuing | 0.000 | 0.260 | 0.315 | 0.435 | 0.435 | 0.435 | 0.435 | - | |
| Number (at Interval start) | 45 | 29 | 26 | 22 | 19 | 19 | 18 | - | |
| Drop out Lack of Efficacy | - | 10 | 3 | 3 | 0 | 0 | 0 | 16 | |
| Censored (total) | - | 6 | 0 | 1 | 3 | 0 | 1 | 11 | |
| **Oxy/APAP (N=43)** | | | | | | | | | |
| Proportion discontinuing | 0.000 | 0.013 | 0.016 | 0.024 | 0.024 | 0.024 | 0.024 | - | **P=0.002** |
| Number (at interval start) | 43 | 32 | 32 | 29 | 29 | 28 | 27 | - | |
| Drop out Lack of Efficacy | - | 0 | 0 | 1 | 0 | 0 | 0 | 1 | |
| Censored (total) | - | 11 | 0 | 2 | 0 | 1 | 1 | 15 | |
| **BTDS (N=46)** | | | | | | | | | |
| Proportion discontinuing | 0.000 | 0.086 | 0.107 | 0.157 | 0.157 | 0.157 | 0.157 | - | **P=0.011** |
| Number (at Interval start) | 46 | 32 | 29 | 25 | 23 | 22 | 22 | - | |
| Drop out Lack of Efficacy | - | 5 | 0 | 2 | 0 | 0 | 0 | 7 | |
| Censored (total) | - | 9 | 3 | 2 | 2 | 1 | 0 | 17 | |

*Proportional hazards model using SAS proc PHREG with covariate correction for center and opioid experience*
*Bar indicates time of dose titration: all BTDS patients started with BTDS 5 and titrated dose on Day 7 and/or Day 14*
*ns = difference not statistically significant (P> 0.05)*
*Bolding indicates statistically significant results*

FIGURE 11

TRANSDERMAL BUPRENORPHINE DOSAGE REGIMEN FOR ANALGESIA

This application claims the benefit of U.S. provisional application No. 60/433,423, filed Dec. 13, 2002, which is incorporated by reference herein in its entirety.

FIELD OF THE INVENTION

The present invention relates to effective dosage regimens for the treatment of chronic pain. The regimen includes administering to a patient a series of transdermal dosage forms including ascending dosages of buprenorphine. It specifically relates to treating pain in elderly patients, including elderly hypertensive subjects, and treating patients with respiratory disease. The invention also relates to treating pain in young and pediatric at risk populations, including for example, those with Chronic Obstructive Pulmonary Disease, reactive airway disease, heart disease, scoliosis, cerebral palsy, juvenile arthritis, or postoperative pain.

BACKGROUND OF THE INVENTION

It has been estimated that approximately 9% of the United States adult population suffers from moderate to severe non-cancer-related chronic pain (American Academy of Pain Medicine, 2001). Chronic pain, which can be defined as pain lasting longer than one month (Bonica, Semin Anesth 1986, 5:82-99), can be described as unrelenting persistent pain that is not amenable to routine pain control methods. As many as 90 million Americans may have suffered from chronic pain, and of these, up to 60 million may have been either partially or totally disabled for periods ranging from a few days to years (Bonica, Semin Anesth 1986, 5:82-99).

Chronic pain states may be classified in several ways. One broad classification distinguishes somatogenic pains, those explicable in terms of physiologic mechanisms, from psychogenic pains, those better understood in psychological terms. A related taxonomy attempts to further distinguish pains by their presumed pathogenesis. For example, nociceptive pain is due to activation of pain-sensitive nerve fibers, either somatic or visceral. When somatic nerves are involved, the pain is typically experienced as aching or pressure-like. Deafferentation pain is due to nerve tissue damage that results in interruption of afferent pathways and can be further differentiated on the basis of response to sympathetic nerve blockade. Finally, psychogenic pains are those due to psychologic source and are not nociceptive or neuropathic.

Pain of long duration loses its adaptive biologic role. Vegetative signs gradually develop, e.g., lassitude, sleep disturbance, decreased appetite, loss of taste for food, weight loss, diminished libido, and constipation. A depressed affect may predominate. Notably, in many patients, the psychological impairment is more disruptive to their life than the continued perception of pain.

The prevalence of chronic pain is particularly high in specific populations, such as the elderly (Mobily, J Aging Health 1994, 6:139-154; Crook et al., Pain 1984, 18:299-314) and post surgical patients (Crook et al., Pain 1984, 18:299-314; Perttunen et al., Acta Anaesthesiol Scand 1999, 43:563-567; Callesen et al., Br J Surg 1999, 86:1528-1531). Among the elderly, it has been estimated that of those who live in the community, 25% to 50% suffer from pain, and of those living in nursing homes, 49% to 83% suffer from pain that interferes with activities of daily living (Ferrel and Ferrell, Compr Ther 1991, 17:53-58; Ferrell, Ann Ther Med 1995, 123:681-687).

A wide range of agents (e.g., nonsteroidal anti-inflammatory drugs, acetaminophen) can be used for the treatment of chronic pain in the elderly and other populations (Brusso and Brose, Ann Rev. Med, 1998, 49:123-133), but opioids remain an important source of pharmacotherapy for this condition (Chemy, J. Oncol Manag 2000, 9:8-15). Opioids may be administered in a variety of dosage forms, including controlled transdermal delivery, which has the potential to increase the convenience of opioid therapy and reduce some of the potential side effects (Ahmedzai, Eur. J. Cancer 1997, 33:58-514; Jeal and Benfield, Drugs 1997, 53:109-138; Mercadente, Cancer 1999, 86:1856-66). Advantages of this approach include application once every several days and avoidance of high peak plasma drug concentrations that may result in adverse events, such as orthostatic hypotension (Dayer et al., Drugs 1997, 53:18-24; Merecadante and Fulfaro, Oncology 1999, 13:215-220, 225).

Transdermal delivery systems in which an opioid analgesic is the active ingredient are commercially available, including, for example, Duragesic for the administration of fentanyl. The Duragesic patch purportedly provides adequate analgesia for up to 48 to 72 hours (2 to 3 days).

In the treatment of the elderly with transdermal dosage forms, the marked changes in the skin of the elderly versus younger individuals should be considered. For example, the thickness of the skin is reduced in the elderly, and sebum secretion is decreased (Seindenari et al., Skin Pharmacol 1994, 7:201-209; Jacobsen et al., J Invest Dermatol 1985, 85:483-485); The number of collagen fibers in the skin declines in old age (Lovell e t al., Br J Dermatol 1987, 117:419-428; Moragas et al., Analyt Quant Cytol Histol 1998, 20:493-499); and the blood flow to the skin is decreased (Rooke et al., J Appl Physiol 1994, 77:11-14; Weiss et al, Age Ageing 1992, 21:237-241).

Buprenorphine is a potent, partial agonist of the μ-opioid receptor that has been shown to be effective to control pain in a wide range of patients when delivered by a number of different routes of administration, including intravenously, epidurally, intrathecally, or sublingually in both young and elderly patients (Inagaki et al., Anesth Analg 1996, 83:530-536; Brema et al., Int J Clin Pharmacol Res 1996, 16:109-116; Capogna et al., Anaesthesia 1988, 43:128-130; Adrianensen et al., Acta Anaesthesiol Belg 1985, 36:33-40; Tauzin-Fin et al., Eur J Anaesthesiol 1998, 15:147-152; Nasar et al., Curr Med Res Opin 1986, 10:251-255). There are several types of transdermal formulations of buprenorphine reported in the literature. See, for example, U.S. Pat. No. 5,240,711 to Hille et al., U.S. Pat. No. 5,225,199 to Hidaka et al., U.S. Pat. No. 5,069,909 to Sharma et al., U.S. Pat. No. 4,806,341 to Chien et al.; U.S. Pat. No. 5,026,556 to Drust et al.; U.S. Pat. No. 5,613,958 to Kochinke et al.; and U.S. Pat. No. 5,968,547 to Reder et al. Transdermal delivery systems of buprenorphine, made by Lohmann Therapie-Systeme GmbH & Co., are currently sold in the European Union under the trademark name TRANSTEC®. These patches contain 20, 30, and 40 mg of buprenorphine, with an approximate delivery or "flux" rate of 35, 52.5, and 70 μg/hr, respectively. The current buprenorphine transdermal systems, however are prescribed for a 7-day dosage period. This may take weeks for a patient in need of an escalated dose to reach a level where the pain relief is effective.

Chronic pain is also a significant problem in the pediatric population, and the physical and psychological symptoms associated with chronic pain may impact overall health and predispose for development of adult chronic pain. In children, chronic pain can be caused by a variety of medical conditions, including juvenile arthritis, cerebral palsy, scoliosis, postoperative, and cancer.

Adolescent and juvenile scoliosis is a spinal abnormality characterized by a lateral curvature in the coronal plane. Techniques for pain management after spinal surgery include intravenous injections, oral medication, patient controlled analgesic delivery systems, and epidural catheter drug delivery. Generally, patients are on a combination of these treatments for 2-4 days after surgery, following which oral analgesics are typically sufficient. However, pain medications may be needed for up to three months after surgery to control residual pain.

Juvenile arthritis (JA) refers to chronic arthritic conditions affecting a pediatric patient, usually under the age of 16 years and often associated with chronic pain. JA covers different conditions where joint inflammation is the major manifestation, further characterized by cycles of flare ups and remissions. Current therapies include treatments to reduce swelling; maintain full movement in the affected joints; relieve pain; and identify, treat, and prevent complications. Medications currently in use include nonsteroidal anti-inflammatory agents (such as ibuprofen and naproxen), methotrexate, sulfasalazine, penicillamine, and hydroxychloroquine. Oral steroid medications are effective, but have adverse side effects with long-term use. Steroid injections into the affected joints may also be effective, however the mode of delivery is often problematic for children. New anti-inflammatory monoclonal antibodies, such as Enbrel, have provided intermittent relief for many treatment resistant patients.

Cerebral palsy is a collective name given to a range of conditions of unknown etiology. For pediatric patients with cerebral palsy, management and prevention of muscle spasm is a common goal. Epidural analgesia is particularly valuable when major orthopedic procedures are performed (Nolan et al., Anesthesia 2000 January; 55(1):32-41). Also, continuous infusions of epidural bupivacaine and fentanyl, a cumbersome procedure, have been used to provide analgesia for children with CP without serious complications, while intermittent bolus epidural morphine was associated with a high incidence of excessive sedation (Brenn et al., Can J Anaesth 1998, 45(12):1156-61). Some of the drugs used in the management of spasms are baclofen and botulinum toxin.

In general, current medications to relieve pain in children include paracetamol, aspirin, non-steroidal anti-inflammatory compositions, opioids (both natural and synthetic) and opioid analogs. While new techniques for pain control in the pediatric population have been proposed, including opioid administration by transdermal or transmucosal absorption, and the use of neuraxial analgesia (Golianu et al., Pediatr Clin North Am 2000, 47(3):559-87), improved methods of long-term pain control are still needed.

Despite advances in the art, there remains a need for methods of effectively treating patients suffering from pain so that effective analgesic levels of buprenorphine are provided for prolonged periods of time without substantially increasing the incidence of adverse side effects, such as nausea or orthostatic hypotension. These concerns are particularly important with respect to providing a safe and effective method of pain management for at risk patients like the elderly, hypertensive patients, patients with respiratory conditions and pediatric patients.

SUMMARY OF THE INVENTION

The present invention provides a specific dosage regimen of buprenorphine that enables effective analgesia or pain relief without eliciting, or at least minimizing, adverse effects such as, but not limited to, nausea, constipation, vomiting, headache, dizziness, and somnolence.

Accordingly, the invention provides a method of treating chronic pain in a patient comprising administering to the patient (1) a first buprenorphine-containing transdermal dosage form for a first dosing period that is no more than 5 days; (2) a second buprenorphine-containing transdermal dosage form for a second dosing period that is no more than 5 days, the second dosage form comprising the same dosage of buprenorphine as, or a greater dosage of buprenorphine than, the first dosage form; and (3) a third buprenorphine-containing transdermal dosage form for a third dosing period, the third dosage form comprising a greater dosage of buprenorphine than the second dosage form.

In specific embodiments, the first, second, and third transdermal dosage forms contain approximately the amounts of buprenorphine set forth in a row in the following table:

| First (mg) | Second (mg) | Third (mg) |
|---|---|---|
| 5 | 5 | 10 |
| 5 | 5 | 20 |
| 5 | 5 | 30 |
| 5 | 10 | 20 |
| 5 | 10 | 30 |
| 5 | 10 | 40 |
| 5 | 20 | 40 |
| 5 | 30 | 40 |
| 10 | 10 | 20 |
| 10 | 10 | 30 |
| 10 | 10 | 40 |
| 10 | 20 | 30 |
| 10 | 20 | 40 |
| 10 | 30 | 40 |
| 20 | 20 | 30 |
| 20 | 20 | 40 |
| 20 | 30 | 40 |

Preferably, the first, second, and third dosing periods are each at least 2 days. More preferably, the first and/or second dosing periods are 5 days, 4 days or 3 days. In a specific embodiment, the first dosage period is 2 days. In another embodiment, the second dosage period is 2 or 3 days. Optionally, the method of the invention further comprises administering a fourth buprenorphine-containing transdermal dosage form for a fourth dosage period at least once after the third dosing period. For example, the fourth dosing period could be 2 days, and the fourth dosage form could comprise 30 or 40 mg buprenorphine.

In one embodiment, the first dosage form comprises 5 mg of buprenorphine. In another embodiment, the second dosage form comprises 10 mg of buprenorphine. In yet other embodiment, the third dosage form comprises 20, 30, or 40 mg of buprenorphine, and the subsequent dosage form comprises 30 or 40 mg of buprenorphine.

One preferred embodiment is where the first dosage form comprises up to 5 mg of buprenorphine, for a dosing period up to 3 days, the second dosage form comprises up to 10 mg of buprenorphine, for a dosing period up to 3 days, and the third dosage form comprises up to 20 mg of buprenorphine, the third dosing period lasting up to 7 days.

In particular embodiments, the patients are elderly or pediatric, elderly hypertensive patients, or patients suffering from pain anticipated to last for at least one week. Conditions where pain is anticipated to last for at least one week include, but are not limited to, those wherein the patient is suffering from osteoarthritis, chronic lower back pain, postoperative pain, or is recovering from extensive trauma. Preferably, the dosage regimen decreases systolic blood pressure by at least about 20 mmHg and/or diastolic blood pressure by at least 10 mmHg. The transdermal administration can be produced by a transdermal system selected from a topical gel, a lotion, an ointment, a transmucosal system, a transmucosal device, and an iontophoretic delivery system.

The invention also provides a method of treating chronic pain in a patient in need thereof, by administering a first, a second, and a third transdermal dosage form of buprenorphine, wherein the third dosage form comprises a higher dosage of buprenorphine than the first and second dosage forms, and wherein the method does not increase the incidence of an adverse event selected from nausea, vomiting, and headache as compared to only administering the same dosage of buprenorphine as the third dosage form. Preferably, the method does not induce syncope. In one embodiment, the first dosage form comprises no more than 5, 10, or 20 mg buprenorphine, the second dosage form comprises no more than 10, 20, or 30 mg buprenorphine and is administered for 3 days, and the third dosage form comprises at least 20, 30, or 40 mg buprenorphine and is administered for at least 2 days. The patient can be an elderly patient, an elderly patient suffering from hypertension, or an elderly patient taking thiazide diuretics for treatment of hypertension. In a particular embodiment, the dosage regimen decreases systolic blood pressure by at least about 20 mmHg and/or diastolic blood pressure by at least 10 mmHg.

The invention also provides a method of treating chronic pain by administering to the patient (1) a first buprenorphine-containing transdermal dosage form for a first dosing period; (2) a second buprenorphine-containing transdermal dosage form for a second dosing period, the second dosage form comprising a greater dosage of buprenorphine than the first dosage form; and (3) a third buprenorphine-containing transdermal dosage form for a third dosing period, the third dosage form comprising a greater dosage of buprenorphine than the second dosage form, wherein the dosing regimen results in a plasma buprenorphine profile characterized by (a) the mean plasma buprenorphine concentration 24 hours after administration being between 10-100 pg/ml, preferably between 20-50 pg/ml; (b) the mean plasma buprenorphine concentration 72 hours after administration being between 25-200 pg/ml, preferably 40-100 pg/ml; (c) the mean plasma buprenorphine concentration 144 hours after administration being between 100-250 pg/ml, preferably 150-200 pg/ml; and (d) the mean plasma buprenorphine concentration 168 hours after administration being between 400-1000 pg/ml, preferably at least 500 pg/ml. In one embodiment, the plasma profile is substantially similar to that depicted in FIG. 1.

In another embodiment, the patient is elderly and/or suffers from hypertension.

In another embodiment, the patient is a pediatric patient suffering from scoliosis, cerebral palsy, juvenile arthritis, cancer, or postoperative pain.

In still other embodiments, the transdermal dosage form is selected from a transdermal dosage article and transdermal dosage composition. The transdermal dosage article can, for example, be a diffusion-driven transdermal system. Alternatively, the transdermal dosage composition can be selected from the group consisting of a topical gel, a lotion, an ointment, a transmucosal system, a transmucosal device, and an iontophoretic delivery system.

BRIEF DESCRIPTION OF THE FIGURES

FIG. 9. Change from baseline in average pain intensity for BTDS and control groups.

FIG. 10. Differences from baseline for "pain right now" between BTDS and control groups.

FIG. 11. Percentage of patients discontinuing due to lack of efficacy at the end of the study.

DETAILED DESCRIPTION OF THE INVENTION

Figure 1:
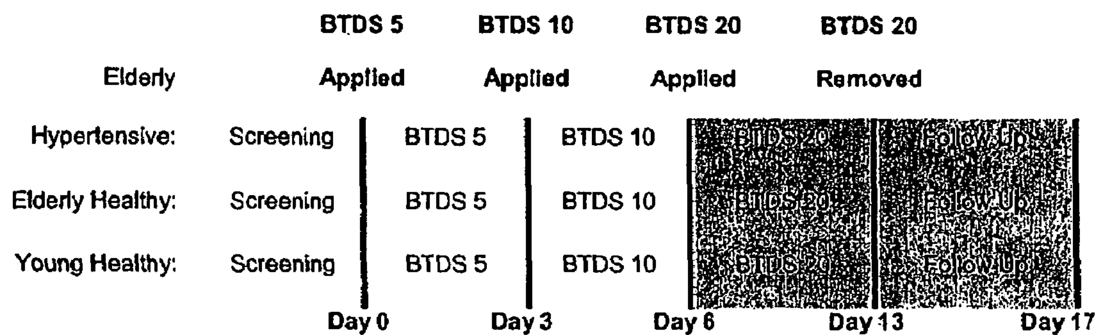
FIG. 1. Study Design.

The present invention provides a method of achieving effective treatment of chronic pain in a patient in need of such treatment quickly, while minimizing certain adverse effects. The invention is based, in part, on the discovery that it is possible to rapidly escalate the dose of transdermal buprenophine to achieve effective analgesia without inducing, or at least minimizing, adverse effects (see, e.g., Example 5). A 7-day transdermal buprenorphine dosage form can delay titration to effective pain therapy, and immediate effective dosages may result in adverse events, especially nausea. Thus, the treatment regimen of the present invention can effectively treat pain, especially pain lasting longer than three days. Such pain can be, for example, postoperative pain, pain caused by cancer or contractive pain, and pediatric pain conditions such as, but not limited to, scoliosis, juvenile arthritis, contractive pain, and cerebral palsy.

The method comprises administering to the patient an analgesically effective amount of buprenorphine in a dosage regimen including administering to the patient a series of transdermal dosage forms with at least one incremental dose of buprenorphine. The dosage regimen of the present invention yields important advantages over prior art dosage regimens for opiods in that it achieves more rapid analgesia than a 7-day dose escalation regimen, while minimizing complications or reducing certain adverse effects. For example, as described in Example 1, a dose-escalation regimen based on titration to BTDS20 in 6 days did not lead to the development of orthostatic hypotension in elderly hypertensive patients treated with a diuretic, nor in healthy, untreated subjects. Orthostatic hypotension is among the known adverse events that can result from the administration of opioid analgesics (Thompson et al., Br J Anaesth 1998, 81:152-154; "Goodman & Gilman's The Pharmacological Basis of Therapeutics," J. G. Hardman (Ed.), McGraw-Hill Professional Publishing, 2001, pp. 530-532). Thus, while not necessarily limited to any particular group or patient population, the present invention provides effective therapy for at risk patients, e.g., patients with impaired cardiovascular reserve such as hypertensive patients. In addition, as described in Example 6, the incidence of nausea, vomiting, and headache in healthy subjects was reduced by dose escalation to BTDS20 within 6 days as compared to direct administration of BTDS20.

The transdermal dosage regimen of the invention also decreased blood pressure in elderly, young, and pediatric patients. The dosage regimen decreased blood pressure without producing significant adverse events that would require discontinuation of use of the regimen. Additionally, pharmacokinetic studies indicated that the plasma profile of the drug in elderly and young subjects was similar, suggesting that no special pharmacokinetic dosage adjustments are needed in specific target population. By contrast, prior studies with a fentanyl transdermal dosage system required removal of the patch due to adverse events, such as respiratory depression, in elderly patients (Thompson et al., Br J Anaesth 1998, 81:152-154). Therefore, the present invention provides a novel method of delivering an opioid analgesic that does not induce adverse events as previously seen with other opioids, while retaining or even increasing, efficacy in treating pain.

The present invention thus provides a more effective method of administering buprenorphine transdermally, increasing the degree of patient compliance with drug therapy and treatment efficacy. The present method reduces the development of adverse events such as, but not limited to, orthostatic hypotension. Therefore, the method increases the degree of patient compliance with drug therapy and treatment efficacy. Notably, the reduction in side effects and minimization of complications (see above, and Examples 1 and 6) does not diminish the primary therapeutic effect: pain control.

The dosage regimen of the present invention may alternatively be described in terms of administration of a "series of transdermal dosage forms comprising at least one incremental dosage of buprenorphine." This refers to the application of at least two transdermal dosage forms to the patient, each having a greater dosage of buprenorphine than the previous dosage form, wherein the dosage of buprenorphine in the series ascends linearly for a predefined number of days, preferably 3 days prior to an increased dosage For example, a series of three transdermal dosage forms may be administered in the dosage regimen, wherein the first dosage form contains 5 mg buprenorphine, the second dosage form contains 10 mg buprenorphine, and the third dosage form contains 20 mg buprenorphine, such that each subsequent dosage form in the series has twice the dosage of buprenorphine than its predecessor. Alternatively, the series of dosage forms may include 20 mg, 30 mg, and 40 mg buprenorphine respectively, or 2 mg, 4 mg, and 8 mg buprenorphine, respectively, or 1 mg, 2 mg, or 3 mg buprenorphine, respectively. Particular dosage regimens (in mg) are 5-5-10, 5-10-10, 5-10-20, 5-20-40, 5-10-30, 5-30-40, 10-10-20, 10-10-30, 10-10-40, 10-20-30, 10-20-40, and 10-30-40. As discussed below, the invention provides kits containing the desired dosage series.

As used herein, "BTDS" means "Buprenorphine Transdermal System", and "BTDS X", wherein "X" is a number higher than zero, means a transdermal dosage form containing X milligrams of buprenorphine. Thus, "BTDS 5" contains about 5 mg buprenorphine. Preferably, a BTDS contains buprenorphine in the form of a base or a salt, more preferably in the form of a base.

The method of the present invention may be administered to any patient in need of pain treatment, including patients in the elderly (age over 65 years), young adult (age between 17 and 45 years), and pediatric (age between birth and 16 years, including age groups often referred to as neonates, infants, children, and adolescent) populations.

The patient may be classified as, but need not be, an at risk patient. In the context of the invention the term "at risk" means that the patient suffers from an existing condition that contraindicates opioid therapy or increases the likelihood of adverse events from such therapy. Such conditions include age; at risk populations may include the elderly and children. The pediatric population specifically includes the school age child, and more specifically infants with at risk conditions, for example bronchopulmonary dysplasia. The at risk patient, especially elderly patient, may be on additional medication to further decrease blood pressure. Such medications include, but are not limited to, diuretics, β-receptor blockers, ACE inhibitors, angiotensin II receptor antagonists, and combinations thereof. In addition, other at risk population groups may include those individuals with heart disease. Specifically, the treatment group may include patients with congestive heart disease, children with right to left shunts, ventricular septal defects, patent ductus arteriosis, status post pulmonary artery shunt, Blalock-Tausig, and Fontane procedures.

The method of the present invention may be administered to any patient in need of pain treatment. The patient may be classified, but need not be, as having a specific medical condition. These medical conditions include but are not limited to by hypertension, scoliosis, cerebral palsy, contractive pain, and other cancers. The patient may, if needed, be on additional medication to further decrease pain. Such medications include, but are not limited to, non-steroidal anti-inflammatory drugs (NSAIDS), acetaminophen (or paracetamol) and immediate-release mu-agonist opioids and/or parenteral opioids, and combinations thereof. The present invention may also be used to supplant existing medications, thereby reducing the need for other types of medication.

An "analgesically effective" amount of an analgesic agent means an amount of agent capable of lowering the level of pain experienced by a patient. The level of pain experienced by a patient can be assessed by use of a visual analog scale (VAS) or a Likert-type scale. A VAS is a straight line with one end of the line representing no pain and the other end of the line representing the worst imaginable pain. Patients are asked to mark on the line where they considered their pain to be at each time point, and the length from no pain to the mark can be related to the length of the full scale. A Likert-type scale is a rating scale, usually in the range of 1 to 5, based on degrees of agreement or disagreement to statements. A similar type of scale, although based on an 11 point scale (ranging from 0 to 10) can also be used. Such pain scales can be applied to visualize an alteration of the level of pain a patient experiences during treatment, e.g., a reduction of the level of pain a patient or a population of patients experiences before and after initiation of a pain therapy.

As to used herein, the term "hypertension" refers to abnormally high arterial blood pressure, when compared to prior blood pressure readings, and the abnormally high value is maintained over a specified time period. Conventionally, the time period is 3-6 months. The increase may be observed in systolic pressure, diastolic pressure, or both. Conventionally, in adults, hypertension is defined as a blood pressure of equal to or greater than 140/90 mm Hg. Blood pressure may be measured by any method known in the art. Such methods include, but are not limited to direct arterial puncture, oscillometry, Doppler ultrasonography, and sphygmomanometry. In usual practice, blood pressure is measured with a stethoscope placed over the brachial artery and a sphygmomanometer cuff placed around the upper arm. The cuff of the sphygmomanometer is inflated by pump until significant occlusion of blood flow is achieved and no pulsation of the blood can be heard. Pressure is released until the first sound of blood flow is heard (first Karatkoff sound), which is the systolic pressure. Pressure is released further until blood flow can no longer be heard, at which point the diastolic pressure reading is recorded (Bate's Guide to Physical Examination and History Taking, $6^{th}$ ed., L. S. Bickley, R. A. Hoekelman, B. Bates, pp. 276-280, Lippincott Williams & Wilkins Publishers, 1995). Blood pressure is measured in millimeters of mercury (mm Hg). Conversely, "hypotension" refers to abnormally low blood pressure relative to population normals.

The phrases "antihypertensive activity" or "decreasing blood pressure" refer to the effect of an active agent to lower the blood pressure of a patient, preferably a patient with hypertension. In one embodiment, the blood pressure is decreased by at least 20 mm Hg for systolic pressure or by at least 10 mm Hg for diastolic pressure for individuals experiencing a drop in blood pressure. In another embodiment, the antihypertensive activity refers to the effect of an active agent to lower the blood pressure by at least 20 mm Hg for systolic pressure and by at least 10 mm Hg for diastolic pressure. The active agent may or may not decrease the blood pressure in a person that does not have hypertension or may not decrease blood pressure in all persons with hypertension. In a preferred embodiment, the transdermal buprenorphine decreases a patient's blood pressure to below 140/90 mm Hg.

The term "orthostatic hypotension" refers to a marked reduction in measured blood pressure that is provoked by standing up quickly from a recumbent position.

As used herein, the term "predefined number of days" refers to the length of time that the dose of the drug is administered to the patient in need prior to initiation of drug therapy. Preferably, the drug is an opioid and more preferably the opioid is buprenorphine. In the context of this invention, the drug is administered for the number of days before initiation of the drug therapy. The predefined number of days may vary between individuals and may be determined by one of ordinary skill in the art using the guidelines discussed within the present application. In a preferred embodiment, the predefined number of days is three days.

The term "adverse event" (AE) or "adverse experience" herein means any untoward medical occurrence in a patient or clinical investigation subject administered a pharmaceutical product and which does not necessarily have to have a causal relationship with this treatment A serious adverse event (experience) or reaction is any untoward medical occurrence that at any dose: results in death, is life-threatening, requires inpatient hospitalization or prolongation of existing hospitalization, results in persistent or significant disability/incapacity, or is a congenital anomaly/birth defect. (Guideline for Industry—Clinical Safety Data Management: Definitions and Standards for Expedited reporting. ICH-E2A, March 1995. World Wide Web (www.) address fda.gov/MedWatch/report/iche2a.pdf, pp. 5-7). Exemplary adverse events in a treatment regimen include, but are not limited to, nausea, constipation, vomiting, headache, dizziness, somnolence, orthostatic hypotension, respiratory depression, choleocystitis, and abdominal pain, (see Table 5 for additional adverse events).

"Partial agonist" herein means an agent that binds to, but does not fully stimulate, a receptor. At both high and low concentration at the receptor, the agent binds and produces a fraction of the total pharmacological activity possible from the receptor. In addition, the agent prevents the binding of a full agonist, thereby blocking the total activity from the receptor. See also Goodman & Gilman's The Pharmacological Basis of Therapeutics, J. G. Hardman (Ed.), McGraw-Hill Professional Publishing, 2001, p. 31-32.

Buprenorphine

The present invention relates to buprenorphine or a pharmaceutically acceptable salt, ether derivative, ester derivative, acid derivative, enantiomer, diasteriomer, racemate, polymorph, or solvate thereof. Pharmacologically, buprenorphine is an opioid partial agonist and shares many of the actions, such as analgesia, of opioid agonists. Partial agonists, generally, include compounds with affinity for a receptor, but unlike full agonists, elicit only a small degree of the pharmacological effect, even if a high proportion of receptors are occupied by the compound. A "ceiling effect" to analgesia (i.e., no additional analgesia with increasing dose) is well documented with respect to buprenorphine in many animal models. It is highly lipophilic and dissociates slowly from opioid receptors. Buprenorphine is considered in the art to be a partial agonist at μ opioid receptors in the central nervous system ("CNS") and peripheral tissues. It is further thought that buprenorphine binds with high affinity to μ and $\kappa_1$ receptors, and, with lower affinity, to δ receptors. The intrinsic agonist activity at the κ receptor seems to be limited and most evidence suggests that buprenorphine has antagonist activity at κ receptors. The lack of κ agonism accounts for buprenorphine's freedom from the dysphoric and psychotomimetic effects often seen with agonist/antagonist drugs. Other studies suggest that the opioid antagonist effects of buprenorphine may be mediated via an interaction with δ opioid receptors.

It is known in the art that buprenorphine binds slowly with, and dissociates slowly from, the μ receptor. The high affinity of buprenorphine for the μ receptor and its slow binding to, and dissociation from, the receptor is thought to possibly account for the prolonged duration of analgesia, and in part, for the limited physical dependence potential observed with the drug. The high affinity binding may also account for the fact that buprenorphine can block the μ agonist effects of other administered opioids.

Like other opioid agonists, buprenorphine produces dose-related analgesia. The exact mechanism has not been fully explained, but analgesia appears to result from a high affinity of buprenorphine for μ and possibly κ opioid receptors in the central nervous system. The drug may also alter the pain threshold (threshold of afferent nerve endings to noxious stimuli). On a weight basis, the analgesic potency of parenteral buprenorphine appears to be about 25 to about 50 times that of parenteral morphine, about 200 times that of pentazocine, and about 600 times that of meperidine.

Salts and Derivatives

Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

The present invention includes prodrugs of the compound of the present invention. Prodrugs include, but are not limited to, functional derivatives of buprenorphine that are readily convertible in vivo into buprenorphine. Conventional procedures for the selection and preparation of suitable prodrug derivatives are described, for example, in "Design of Prodrugs", ed. H. Bundgaard, Elsevier, 1985.

Transdermal Dosage Forms

Transdermal dosage forms are convenient dosage forms for delivering many different active therapeutically effective agents, including but not limited to analgesics, such as for example, opioid analgesics. Typical opioid analgesics include, but are not limited to, fentanyl, buprenorphine, etorphines, and other high potency narcotics. Transdermal dosage forms are particularly useful for timed release and sustained release of active agents.

Transdermal dosage forms may be classified into transdermal dosage articles and transdermal dosage compositions. The most common transdermal dosage article is a diffusion-driven transdermal system (transdermal patch) using either a fluid reservoir or a drug-in-adhesive matrix system. Transdermal dosage compositions include, but are not limited to, topical gels, lotions, ointments, transmucosal systems and devices, and iontophoretic (electrical diffusion) delivery systems. Preferably, the transdermal dosage form is a transdermal patch.

The pharmaceutical compositions are formulated as transdermal dosage forms, such as a diffusion-driven transdermal system (transdermal patch) using either a fluid reservoir or a drug-in-adhesive matrix system, topical gels, lotions, ointments, transmucosal systems and devices, and iontophoretic (electrical diffusion) delivery system. The transdermal dosage form is used in the dosage regimen of the present invention for timed release and sustained release of buprenorphine.

Transdermal dosage forms used in accordance with the invention preferably include a backing layer made of pharmaceutically acceptable material which is impermeable to the buprenorphine. The backing layer preferably serves as a protective cover for the active agent, e.g. buprenorphine and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof. Exemplary materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable crosslinking agent. Suitable crosslinking agents include, e.g., tetrapropoxy silane. Preferred transdermal delivery systems used in accordance with the methods of the present invention include an adhesive layer to affix the dosage form to the skin of the patient for a desired period of administration, e.g., about 2 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g., surgical tape. Adhesion of the dosage form to the skin of the patient can be achieved solely by the adhesive layer of the dosage form or in connection with a peripheral adhesive source, such as surgical tape, but the dosage form should preferably be adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the buprenorphine into the blood stream of the patient. A non-limiting list of permeation enhancing agents includes polyethylene glycols, surfactants, and the like.

Alternatively, permeation of buprenorphine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of buprenorphine such as the use of iontophoretic means are also contemplated to be within the scope of the present invention.

A preferred transdermal dosage form which may be used in accordance with the present invention includes a non-permeable backing layer made, for example, of polyester; an adhesive layer made, for example of a polyacrylate; and a matrix containing the buprenorphine and other desirable pharmaceutical aids such as softeners, permeability enhancers, viscosity agents and the like.

The active agent, buprenorphine, may be included in the device in a drug reservoir, drug matrix or drug/adhesive layer. This area of the patch, and the amount of active per unit area determine the limit dose, as one of ordinary skill in the art can readily determine.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol which can also be etherified by polyethylene glycols.

A buprenorphine solvent may also be included in the transdermal delivery systems of the present invention. Preferably, the solvents dissolve the buprenorphine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polyletra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage forms used in accordance with the invention and the type of device used are not considered critical to the method of the invention, provided that the device delivers the active agent, e.g. buprenorphine, for the desired time period and at the desired flux rate and/or the desired delivery rate of the transdermal dosage form.

Certain preferred transdermal dosage forms for use in accordance with the present invention are described in U.S. Pat. No. 5,240,711 to Hille, et. al.; (assigned to LTS Lohmann Therapie-Systeme GmbH & Co.), hereby incorporated by reference. Such buprenorphine transdermal delivery systems may be a laminated composite having an impermeable backing layer containing buprenorphine, and optionally, a permeation enhancer combined with a pressure-sensitive adhesive. A preferred transdermal dosage form in accordance with the U.S. Pat. No. 5,240,711 patent includes: (i) a polyester backing layer which is impermeable to buprenorphine; (ii) a polyacrylate adhesive layer; (iii) a separating polyester layer; and (iv) a matrix containing buprenorphine, a solvent for the buprenorphine, a softener and a polyacrylate adhesive. The buprenorphine solvent may or may not be present in the final formulation. The transdermal delivery device described therein includes a backing layer which is impermeable to the active substance, a pressure-sensitive adhesive reservoir layer and optionally, a removable protective layer. Preferably, the reservoir layer includes about 10 to about 95% (by weight) polymeric material, about 0.1 to about 40% (by weight) softener, about 0.1 to about 30% (by weight) buprenorphine. A solvent for the buprenorphine base or pharmaceutically acceptable salt thereof may be included as about 0.1 to about 30% (by weight).

The dosing regimen of the present invention comprises several discrete dosing periods. A dosing period is the time during which one of the transdermal dosage forms in the series is administered to the patient, and the dosing regimen will consist of a separate dosing period for administration of each transdermal dosage form in the series. Thus, for example, the first transdermal dosage form in the series may be worn by the patient for three consecutive days. The patch may, for example, be placed at the mid-axillary line at the fifth intercostal space. Upon removal, the second dosage form may then be worn by the patient for another three consecutive days, and thereafter, the third dosage form may be worn by the patient for another seven days. In a preferred embodiment, the total treatment period of the dosing regimen is six days until the desired dose, i.e., the third dose level, is attained. This dose can then be maintained indefinitely. If an increase in dosage is required, then the dosage may be increased at an appropriate interval, e.g., every three days.

The dosage forms of the present invention may also include one or more inactivating agents. The term "inactivating agent" refers to a compound that inactivates or crosslinks the active agent, in order to decrease the abuse potential of the transdermal dosage form. Non limiting examples of a inactivating agents include, but are not limited to, polymerizing agents, photinitiators, and formalin. Examples of polymerizing agents include diisocyanates, peroxides, diimides, diols, triols, epoxides, cyanoacrylates, and UV activated monomers.

In a preferred embodiment, the method of the present invention is used to treat chronic pain in the elderly, e.g., a patient aged 65 or older. In another preferred embodiment, the method of the present invention is used to treat chronic pain in pediatric populations.

The method of the present invention preferably administers buprenorphine in a way that achieves a gradual increase in the plasma concentration of buprenorphine in the patient. In a preferred embodiment, the plasma profile achieved by the method of the present invention may be described as follows:

(a) the mean plasma buprenorphine concentration 24 hours after administration is between 10-100 pg/ml, preferably 20-50 pg/ml;

(b) the mean plasma buprenorphine concentration 72 hours after administration is between 25-200 pg/ml, preferably 40-100 pg/ml;

(c) the mean plasma buprenorphine concentration 144 hours after administration is between 100-250 pg/ml, preferably 150-200 pg/ml; and (d) the mean plasma buprenorphine concentration 168 hours after administration is between 400-1000 pg/ml, preferably at least 500 pg/ml, or higher depending on the patient's need.

Figure 2:
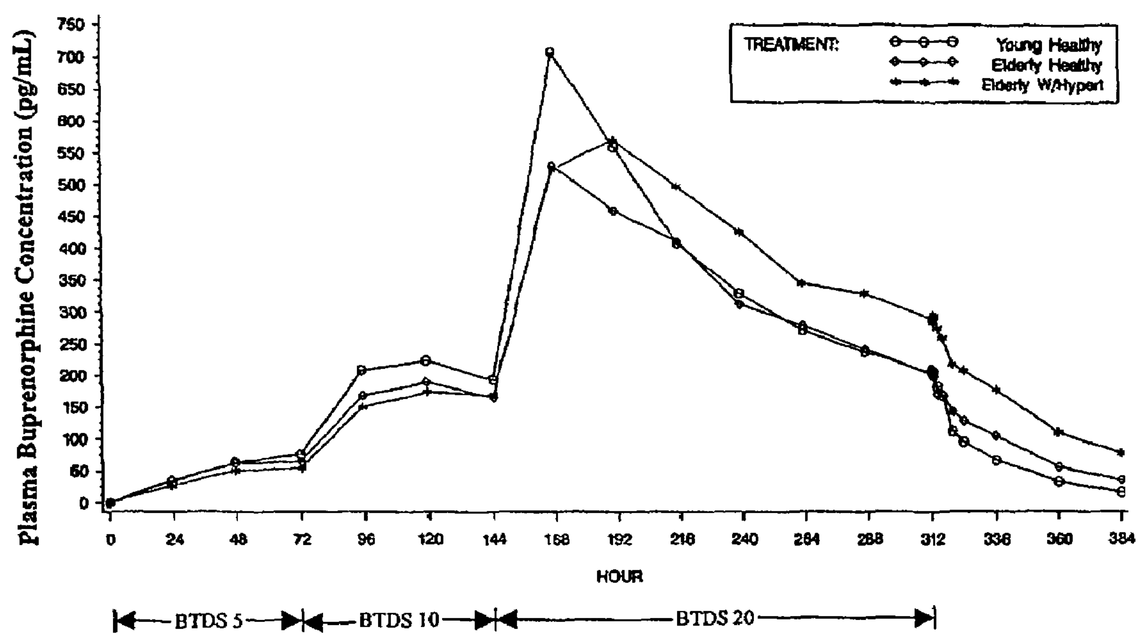
FIG. 2. Plasma concentration versus time curves for buprenorphine after application of BTDS 5 (0-72) hours), BTDS 10 (72-144 hours), and BTDS 20 (144-312 hours).

In a preferred embodiment, the method of the present invention achieves a plasma profile that is substantially similar to that depicted in FIG. 2. "Substantially similar" refers to a profile of which the maximum plasma concentration ($c_{max}$) or area under the plasma concentration-time course profile (AUC) differs no more than 30% from that of a reference profile depicted in FIG. 2. Preferably, the maximum plasma concentration ($c_{max}$) and/or area under the plasma concentration-time course profile (AUC) differs no more than 20%, even more preferably no more than 10%, from that of a reference profile depicted in FIG. 2. Alternatively, the plasma profile is bioequivalent to the reference profile, as determined according to Food and Drug Administration (FDA) guidelines (see 21 C.F.R. §320, and "Guidance for Industry—Statistical Approaches to Establishing Bioequivalence" U.S. Dept. of Health and Human Services, FDA, and CDER, January 2001).

Topical preparations typically contain a suspending agent and optionally, an antifoaming agent. Such topical preparations may be liquid drenches, alcoholic solutions, topical cleansers, cleansing creams, skin gels, skin lotions, and shampoos in cream or gel formulations (including, but not limited to aqueous solutions and suspensions).

The compound of the present invention also can be administered in the form of liposome delivery systems, such as small unilamellar vesicles, large unilamellar vesicles and multilamellar vesicles that may be included in the transdermal article or transdermal composition. Liposomes can be formed from a variety of phospholipids, such as cholesterol, stearylamine or phosphatidylcholines.

The transdermal dosage form may be formulated by any method known in the art and may be administered as suggested. Such formulations are described in U.S. Pat. Nos. 4,806,341; 5,240,711; and 5,968,547.

Patient Population

As described herein, the dose escalation regimen of the invention can be applied for pain therapy of patients in any age group, including pediatric patients. The pediatric patients can suffer from chronic pain symptoms from conditions including, but not limited to scoliosis, juvenile arthritis, and contractive pain, sickle cell pain and prolonged (greater than 3 days) postoperative pain.

The particular BTDS administration to the pediatric population provides rapid dosage escalation without the discomfort of needles associated with injections, or with oral medications. Furthermore, assessment of a child's pain may be difficult due to a child's inability to relay the discomfort, and thus the treatment may be delayed. Patient compliance is also increased in that the application of the BTDS patch will likely be placement upon the back, thereby avoiding the removal of the medication.

In the present invention, dosage regimens for the pediatric population can be closely aligned with those of the adult population, since weight differences can be compensated by differences in absorption and metabolism in achieving a target plasma level. Children may generally require approximately 30-40% more on a per-pound basis to achieve the same blood levels of the opioid. For example, a 25 kg (55 lb) child using BTDS 20 could achieve approximately similar plasma levels as a 50 kg adult using the same BTDS 20. Therefore, in a preferred embodiment, the dosage schemes for pediatric patients are the same as that of adults.

Administration

The unit dosage forms of the present invention are administered to a patient suffering from chronic pain, preferably a human being. In a preferred embodiment, the patient is elderly. In another preferred embodiment, the patient is pediatric. The unit dosage forms of the present invention may be administered at the defined dosing regimen in order to obtain optimal activity while minimizing any potential toxicity. For example, the method involves administering to the patient an analgesic effective amount of buprenorphine in a dosage regimen comprising administering to the patient a series of transdermal dosage forms comprising graduated and ascending dosages of buprenorphine. Preferably, the dosage regimen comprises the steps of:

(a) administering to the patient a first buprenorphine-containing transdermal dosage form for a first dosing period;

(b) administering to the patient a second buprenorphine-containing transdermal dosage form for a second dosing period, wherein the second dosage form comprises the same or a greater dosage of buprenorphine than the first dosage form; and (c) administering to the patient a third buprenorphine-containing transdermal dosage form for a third dosing period, wherein the third dosage form comprises a greater dosage of buprenorphine than the second dosage form.

In a specific embodiment the first dosage form comprises up to 5 mg buprenorphine, the first dosing period is at least about 2 days, the second dosage form comprises up to 10 mg buprenorphine, the second dosing period is at least about 3 days; the third dosage form comprises up to 20 mg buprenorphine, and the third dosing period is at least about 2 days. In another specific embodiments, the first and second dosing periods are less than about 7 days each, preferably less than about 5 days, and even more preferably no more than about 3 days.

In another embodiment, subsequent dosages may be administered. For example, if the target analgesia level is attained with the third dosing period, the third dosage form can be continually administered for an indefinite period of time, changing patches with a frequency extending from about every 2 days to about weekly. If the target analgesia level is not attained with the third dosing period, subsequent dosage forms can be used incrementally starting with 30 mg buprenorphine and 40 mg buprenorphine load.

The dosage of the compound of the present invention may vary according to a variety of factors such as underlying disease states, the individual's condition, weight, sex and age and the mode of administration. The dosage predefined interval or regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the absorption, distribution, metabolism, and excretion of a drug.

The composition or dosage form of the invention, when administered as a transdermal dosage form, may be provided to any body part as determined by one of ordinary skill in the art. For example, the composition or dosage form may be provided to the arm, leg or chest of the patient. In the preferred embodiment for children, the placement is preferably on the back to prevent the removal of the transdermal unit. Repeated doses may or may not be administered to the same location each time.

Generally, topical preparations contain from about 0.01 to about 100% by weight and preferably from about 3 to about 80% by weight of the compound, based upon 100% total weight of the topical preparation. Generally, transdermal dosage forms contain from about 0.01 to about 100% by weight and preferably from about 3 to about 50% by weight of the compound, based upon 100% total weight of the dosage.

The dosage forms used in the method of the present invention may be administered alone or in combination with other active agents. For combination treatment with more than one active agent, where the active agents are in separate dosage formulations, the active agents can be administered concurrently, or they each can be administered at separately staggered times. The dosage amount may be adjusted when combined with other active agents as described above to achieve desired effects. On the other hand, unit dosage forms of these various active agents may be independently optimized and combined to achieve a synergistic result wherein the pathology is reduced more than it would be if either active agent were used alone.

The particular BTDS administration to the pediatric population is advantageous in that the rapid dosage escalation occurs without the discomfort of needles associated with injections, or with oral medications. In the present invention, the time to optimal pain relief is greatly decreased. Patient compliance is also increased in that the application of the BTDS patch will likely be placement upon the back, thereby avoiding the removal of the medication.

Kits

The present invention also provides an embodiment wherein the components for practicing the invention can be conveniently provided in a kit form. In its simplest embodiment, a kit of the invention provides a set number of buprenorphine patches at set dosages, wherein the dosages are set according to the needs of the patient. Each kit will include the appropriate dosage regimen selected from the following table.

| Amount of Buprenorphine per Transdermal Dosage Form (mg) | | |
|---|---|---|
| First | Second | Third |
| 5 | 5 | 10 |
| 5 | 5 | 20 |
| 5 | 5 | 30 |
| 5 | 10 | 20 |
| 5 | 10 | 30 |
| 5 | 10 | 40 |
| 5 | 20 | 40 |
| 5 | 30 | 40 |
| 10 | 10 | 20 |
| 10 | 10 | 30 |
| 10 | 10 | 40 |
| 10 | 20 | 30 |
| 10 | 20 | 40 |
| 10 | 30 | 40 |
| 20 | 20 | 30 |
| 20 | 20 | 40 |
| 20 | 30 | 40 |

In a preferred embodiment, the dosage regimen is 5 mg, 10 mg, and 20 mg. Instructions on how to apply the patch, storage of the unit, and details of the treatment regimen Are also included.

In a further embodiment, the kit will include a disposal container or device for disposal of used buprenorphine patches. Such containers or devices will be used to prevent or limit potential abuse of the drug within the patch. As used herein, the term container has its broadest meaning, i.e., any receptacle for holding material.

A kit of the invention preferably includes packaging and instructions for its use, e.g., on the packing or package insert. The buprenorphine patches within the kit may be coded (i.e., color, numerical by day, or numerical by dose, etc.) for the patient. The patient would have the BTDS applied in the prescribed sequence and have access to immediate release rescue medication as needed until the pain relief is judged to be sufficient by the patient.

EXAMPLES

The present invention will be better understood by reference to the following Examples, which are provided as exemplary of the invention, and not by way of limitation.

Example 1

Physiologic Effects of BTDS Dosing Regimen in Elderly and Elderly Hypertensive Patients Receiving Thiazide Diuretics The purpose of this study was to evaluate the physiologic effects of BTDS dose escalation in the elderly and elderly hypertensive subjects receiving thiazide diuretics.

Subject Selection

A. Elderly Hypertensive Subjects: male or female hypertensive subjects, aged 65-80 years, body weight ranging from 70-94 kg (males) and 55 to 81 kg (females). Except for hypertension, patients were free of significant abnormal medical history, as evidenced by baseline physical examination, hematology, blood chemistries, urinalysis, ECG, and vital signs. Females had to be postmenopausal, i.e., at least one year without menses, or surgically sterile. Blood pressure and antihypertensive medication were to be stable for at least 2 months prior to entry. Blood pressure was controlled with thiazide diuretics alone or in combination with any other single agent.
B. Elderly healthy subjects: male or female elderly subjects, aged 65-74 years, inclusive, body weight ranging from 70-94 kg (males) and 55 to 81 kg (females). Patients were free of significant abnormal medical history, as evidenced by baseline physical examination, hematology, blood chemistries, urinalysis, ECG, and vital signs. Females had to be postmenopausal, i.e., at least one year without menses, or surgically sterile.
C. Young healthy subjects: male or female subjects, aged 21-40 years, body weight ranging from 70-94 kg (males) and 55 to 81 kg (females). Patients were free of significant abnormal medical history, as evidenced by baseline physical examination, hematology, blood chemistries, urinalysis, ECG, and vital signs. Females had to have a negative serum pregnancy testing during screening visit and at predose. Barrier or IUD contraception with additional spermicidal foam or jelly was to be used from screening until discharge from the study.

Exclusion Criteria

1. Any history of hypersensitivity to opioids or to psychotropic or hypnotic drugs.
2. History of seizures, presyncope, or syncope.
3. Any medical or surgical conditions that might significantly interfere with transdermal absorption, distribution, metabolism or excretion of buprenorphine.
4. Any concomitant medical conditions requiring ongoing prescription or over-the-counter medication, except for hormone replacement therapy (systemic or local) in elderly female subjects and antihypertensive medications in elderly hypertensive subjects.
5. Use of opioid-containing medication for more than 7 days within past 3 months.
6. History of drug or alcohol abuse in the past 2 years.
7. Documented, ongoing, clinically significant cardiovascular, pulmonary, endocrine, neurologic, metabolic, or psychiatric disease.
8. History of frequent nausea or emesis regardless of etiology.
9. Participation in a clinical study during the 30 days prior to enrollment in this study.
10. Any significant illness during the 4 weeks preceding entry into this study.
11. Use of any medication, including vitamin and/or mineral supplements, during the 7 days preceding study medication application.
12. Refusal to abstain from food and caffeine-containing beverages from 8 hours preceding study drug administration to 4 hours after the start of study drug administration.
13. Positive prestudy (screening) or immediate premedication blood alcohol, urine drug screen or serum pregnancy test.
14. Current use of tobacco products.
15. Intake of alcohol >60 gms per day.
16. Consumption of alcoholic beverages within 48 hours of study medication application or at any time during the study.
17. Blood or blood products donated in the past 6 weeks prior to study medication application.
18. Positive HIV (Eliza) and/or Hepatitis B (HBsAg).

Methods

Subjects were administered BTDS 5 from day 0 to day 3, BTDS 10 from day 3 to day 6, and BTDS 20 from day 6 to day 13. After day 13, patients were monitored for an additional 4 days (day 17).

Vital signs were measured as follows:

1. 0, 1, 4, 8, 12, 24 hr. prior to application of BTDS 5;
2. Day 0 and 3, 30 min. prior to application of BTDS 5 and 10 and 1, 2, 4, 8, 12, 20, 23, 36, 47, and 60 hr. after the application of BTDS 5 and BTDS 10;
3. Day 6, 30 min. prior to application of BTDS 20 and 1, 2, 4, 8, 12, 20, 23, 36, 47, 60, 71, 84, 95, 108, 119, 132, 143, 156 and 164 hr. after application of BTDS 20; and
4. Day 13, 0.25, 0.50, 0.75, 1, 2, 4, 8, 12, 24, 48, and 72 hr. after removal of BTDS 20.

The vital signs tested included blood pressure (subjects remained supine for 5 minutes, then had their blood pressure measured; thereafter subjects stood, and blood pressure was measured after 1 minute of standing and after 2 minutes standing), pulse (bpm, measured 5 minutes supine, 1 minute standing, and 2 minutes standing), respiratory rate (breaths/minute), and transcutaneous oxygen saturation ($SaO_2$).

Physiologic Measurements. Blood pressure (mmHg): At each scheduled assessment time, subjects remained supine for 5 minutes, then had their BP measured. Subjects then stood, and BP was measured after 1 minute of standing and after 2 minutes of standing.

Pulse (bpm): Pulse was measured at 5 minutes supine, 1 minute standing, and 2 minutes standing.

Transcutaneous oxygen saturation ($SaO_2$): Transcutaneous $SaO_2$ was measured by pulse oximetry using a fingertip sensor that quantified $SaO_2$ by infrared spectrophotometry.

Pharmacokinetic sampling was conducted as follows:

(1) 0, 23, 47 hr. after application of BTDS 5 and BTDS 10;

(2) 0, 23, 47, 71, 95, 119, and 143 hr. after application of BTDS 20; and (3) 0.25, 0.50, 0.75, 1, 2, 4, 8, 12, 24, 48, and 72 hr. after removal of BTDS 20.

Assessment of Local Reactions at BTDS Application Sites. Assessment of skin for reactions at the B TDS application site were made before initial system application and at each BTDS removal. The appearance of the skin at the BTDS application site was rated for erythema and edema using rating scales in which erythema ranged from 0 (no visible redness) to 5 (dark red discoloration of the skin) and edema varied from 0 (no visible reaction) to 5 (severe swelling extending more than 1 mm in diameter and protruding over the edges of the system).

Clinical Laboratory Tests. Laboratory tests were carried out on blood and urine samples obtained at screening and at study completion (day 15). Blood samples were analyzed for hematology and chemistry, and urinalysis assessments included color, turbidity, specific gravity, glucose, albumin, bile (urobilinogen), pH, acetone (ketone), and microscopic examination.

Physical Examination and ECG. A standard physical examination and 12-lead ECG were conducted at screening and study completion. Vital signs were taken at these times in addition to those taken for pharmacodynamic evaluation.

Buprenorphine/Norbuprenorphine Assays. The pharmacokinetic analysis included assaying plasma samples for concentrations of buprenorphine and norbuprenorphine. Norbuprenorphine is the major known Phase I metabolite of buprenorphine and has lower pharmacologic activity than its parent compound.

Briefly, buprenorphine and norbuprenorphine, and the internal standards deuterated d4-buprenorphine and deuterated d9-norbuprenorphine (Radian Corporation, Austin, Tex.) were measured by Liquid Chromatography-Electrospray/Mass Spectrometry/Mass Spectrometry (LC-ESI/MS/MS). For general descriptions of these technologies, see Huang et al., Anal Chem 1990, 62:713A-725A.; Heel et al., Curr Ther 1979, 5:29-33.; Watson et al., 1982???; Adriansensen et al., Acta Anaesthesiol Belg 1985, 36:33-40; Lewis and Walter, "Buprenorphine: An Alternative Treatment For Opioid Dependence" National Institute on Drug Abuse, Monograph series; Hand et al., 1989; Tebbett, 1985; and Blom et al., 1985. Internal standards were spiked into human plasma prior to sample preparation by pipetting appropriate volumes of d4-buprenorphine/d9-norbuprenorphine solutions into human plasma treated with EDTA to prevent coagulation.

Solid Phase Extraction (SPE) was used to isolate the two compounds of interest from 0.5 mL human plasma samples. Before extraction, all patient samples, standards, and controls were thawed at 37° C., vortexed, and centrifuged at 3000 rpm for at least 15 minutes. Buffer (8 mM ammonium acetate) and internal standards were added to each plasma sample, including controls and standards (i.e., samples containing known amounts of buprenorphine and/or norbuprenorphine). Each sample, standard, and control was then subjected to an extraction procedure using either Packard MultiProbe IIEX (Packard, Meriden, Conn.) or Tomtec Qadra (Tomtech, Hamden, Conn.), wherein the analytes of interest were absorbed by a stationary phase, followed by washing to remove matrix material and elution to recovery the analytes. The eluent was evaporated to dryness under a stream of nitrogen gas at 45° C., and thereafter reconstituted in 9:1 acetonitrile:ammonium acetate (8 mM).

A High Performance Liquid Chromatography (HPLC) system based on a reverse-phase SB-C18 column (2.1 mm ID×50 mm, 5 u particle size; Hewlett-Packard, Wilmington, Del.) using an acetonitrile:ammonium acetate:methanol mobile phase, was applied to separate the components in each sample prior to MS.

The MS system consisted of a Micromass Qattro LC Mass Spectrometer equipped with an ESI source (Micromass Inc., Beverly, Mass.) and operated in Multiple Reaction Monitoring Mode (MRM). Qantitation was performed using a calibration curve based on the peak area ratios of buprenorphine to d4-buprenorphine, and norbuprenorphine to d9-norbuprenorphine. The transition processes from precursor or molecular ion(s) to product ion(s) were used for both analytes to enhance the selectivity and sensitivity for buprenorphine and norbuprenorphine analysis. The transitions used were 468.1 to 55.1 (for buprenorphine), 472.4 to 59.1 (for d4-buprenorphine), 414.1 to 101.0 (for norbuprenorphine), and 423.1 to 110.0 (for d9-norbuprenorphine). The exact transition of precursor to product ion can be fine-tuned based on the mass-tune report.

The Micromass MassLynx software was used to integrate the chromatographic peaks from the MS and determine the peak area ratios of buprenorphine/d4-buprenorphine and norbuprenorphine/d9-norbuprenorphine. The ratios of the areas were determined for each plasma standard, sample, and control. The standard peak area ratios were then used to prepare a calibration curve based on a weighted ($1/x^2$) linear regression. Sample and control concentrations were calculated from the regression line in pg/mL. The quantitation limit of the method was determined to be 25 pg/mL in human plasma for both analytes, with a concentration range from 25 to 600 pg/mL in human plasma.

Pharmacokinetic Metrics. The following pharmacokinetic metrics were estimated from plasma buprenorphine and plasma norbuprenorphine concentrations following treatment with BTDS:

$AUC_t$ (pg·h/mL). The area under the plasma concentration-time course profile from time=0 (system application) to the last quantifiable concentration was estimated using the linear trapezoidal rule as follows:

$$AUC_t = \sum_{i=1}^{n-1} \left[ \frac{C_{i+1} + C_i}{2} (t_{i+1} - t_i) \right]$$

where $c_i$ is the concentration in the $i^{th}$ sample, $t_i$ is the time of the $i^{th}$ sample from dosing, and n is the number of available samples up to and including the last quantifiable concentration.

$AUC_\infty$ (pg·h/mL)—The area under the plasma concentration-time course profile from time=0 (dosing) to infinity was estimated as:

$$AUC_\infty = AUC_t + \frac{C_t}{\lambda_z}$$

where $C_t$ was the last quantifiable concentration and $\lambda_z$ was the negative slope of the apparent terminal phase of the log-transformed profile.

$C_{max}$ (pg/mL)—Measured plasma concentrations of buprenorphine and norbuprenorphine versus sampling time were plotted in plasma concentration-time course profiles for each individual. The maximum concentration of each substance was taken from each respective profile. The average maximum concentration of each substance was calculated as the arithmetic mean of all individual values.

$t_{max}$ (h)—The time from dosing to the maximum observed concentration was taken directly from the plasma concentration-time course profile. The average time from dosing to the maximum observed concentration was calculated as the arithmetic mean of all individual values.

$t_{1/2}$ (h)—The apparent terminal half-life was estimated as follows:

$$t_{1/2} = \frac{\ln(2)}{\lambda_z}$$

wherein $\lambda_z$ is the first order rate constant associated with the terminal (log-linear) portion of the curve. This was estimated by linear regression of time versus log concentration. The apparent terminal half-life was considered reportable if the following criteria were met:

The observed data points must be on the terminal log-linear phase.

At least 3 data points per determination

Coefficient of determination ($R^2$)>0.85.

If the individual time-course data set failed to meet the above criteria, the $t_{1/2}$ was reported as not estimable.

Between-group comparison within each interval for average supine BP was performed using an analysis of covariance (ANCOVA) model with the average supine blood pressure as the response variable, group as predictor, and baseline average supine blood pressure as covariate. Pairwise comparisons between the 2 elderly groups and the group of young healthy subjects were also performed. All other PD variables were analyzed in the same way.

Pharmacokinetic metrics were log-transformed for analyses. For log-transformed variables, exponentiating the differences and the limits of the confidence intervals yielded corresponding mean ratio and confidence intervals in the original scale. Between-group comparison of pharmacokinetic metrics was performed using an analysis of variance (ANOVA) model. Pairwise comparisons between the 2 elderly groups and the group of young healthy subjects were performed. Statistical significance was assessed at the 5% level with no adjustment for Type I error due to multiple comparisons. Confidence intervals (90%) were estimated around ratios (elderly healthy/young healthy and elderly hypertensive/young healthy) of the least squares means of $AUC_t$, $AUC_\infty$, and $C_{max}$.

Statistical Methods. Between-group comparison within each interval for average supine BP was performed using an analysis of covariance (ANCOVA) model with the average supine BP as the response variable, group as predictor, and baseline average supine BP as covariate. Pairwise comparisons between the 2 elderly groups and the group of young healthy subjects were also performed. All other PD variables were analyzed in the same way.

Pharmacokinetic metrics were log-transformed for analyses. For log-transformed variables, exponentiating the differences and the limits of the confidence intervals yielded corresponding mean ratio and confidence intervals in the original scale. Between-group comparison of pharmacokinetic metrics was performed using an analysis of variance (ANOVA) model. Pairwise comparisons between the 2 elderly groups and the group of young healthy subjects were performed. Statistical significance was assessed at the 5% level with no adjustment for Type I error due to multiple comparisons. Confidence intervals (90%) were estimated around ratios (elderly healthy/young healthy and elderly hypertensive/young healthy) of the least squares means of $AUC_t$, $AUC_\infty$, and $C_{max}$.

Results and Discussion

Physiological and safety results are presented in Tables 1-6 and FIGS. 1-5.

Subject Demographics and Baseline Disposition. Thirty-six subjects were enrolled in the study: 12 young healthy subjects (aged 21 to 40 years, mean age 29 years), 13 elderly healthy subjects (aged 65 to 74 years, mean age 68 years), and 11 elderly subjects with hypertension (aged 65 to 80 years, mean age 71 years). All subjects were evaluable for pharmacodynarnic and safety assessments, and 32 provided data for pharmacokinetic analysis. Demographic and baseline physiologic characteristics for the subjects are summarized in Table 1.

TABLE 1

Baseline demographic characteristics and hemodynamic and respiratory parameters for the 3 subject groups

| | Young Healthy (n = 12) | Elderly Healthy (n = 13) | Elderly Hypertensive (n = 11) |
|---|---|---|---|
| Mean age (yrs; (range)) | 29 (21-40) | 68 (65-74) | 71 (65-80) |
| Weight (kg; (range)) | 72 (50-93) | 74 (50-85) | 75 (57-91) |
| Gender (%) | | | |
| Male | 10 (83%) | 8 (62%) | 3 (27%) |
| Female | 2 (17%) | 5 (38%) | 8 (73%) |
| Race (%) | | | |
| White | 9 (75%) | 12 (92%) | 10 (91%) |
| Hispanic | 2 (17%) | 1 (8%) | 1 (9%) |
| Other | 1 (8%) | 0 | 0 |
| Mean (SE) blood pressure (mm Hg) 5-minute supine | | | |
| Systolic | 114.7 (2.6) | 128.7 (4.5) | 128.2 (3.1) |
| Diastolic | 67.9 (1.9) | 75.3 (1.9) | 71.6 (1.4) |
| 2-minute standing | | | |
| Systolic | 116.3 (3.0) | 129.7 (3.6) | 132.5 (3.5) |
| Diastolic | 74.9 (2.1) | 79.4 (2.6) | 82.7 (2.9) |
| Mean (SE) pulse (bpm) | | | |
| 5-minute supine | 57.2 (2.3) | 66.1 (2.6) | 65.8 (2.8) |
| 2-minute standing | 73.8 (2.9) | 78.3 (3.2) | 78.3 (3.2) |
| Mean (SE) RR (breaths/min) | 15.5 (1.0) | 13.2 (0.5) | 12.9 (0.6) |
| Mean (SE) % $SaO_2$ | 95.4 (0.6) | 93.4 (1.3) | 93.9 (0.7) |

Pharmacodynamic Results

Orthostatic Changes in Blood Pressure and Pulse Rate. Table 2 summarizes differences between 5-minute supine and 2-minute upright blood pressure and pulse rate readings taken 30 minutes prior to initial BTDS application (baseline), 4 to 8 hours after each dosage escalation, and 3.5 hours after removal of BTDS 20 on day 13.

TABLE 2

Orthostatic changes[a] in blood pressure and pulse rate for subjects in the 3 groups with application of BTDS[b]

| | Mean Change (SE) | | | 90% CI[f] | |
|---|---|---|---|---|---|
| | Young Healthy (n = 12) | Elderly Healthy (n = 13) | Elderly Hypertensive (n = 11) | Young Minus Healthy Elderly | Young Minus Hypertensive Elderly |
| **Blood pressure** | | | | | |
| Baseline | | | | | |
| Systolic (mm Hg) | 1.67 (2.81) | 1.00 (2.60) | 4.27 (2.64) | — | — |
| Distolic (mm Hg) | 7.00 (2.25) | 4.08 (2.89) | 11.09 (2.05) | — | — |
| Application 1 (BTDS 5) | | | | | |
| Systolic (mm Hg) | 3.08 (1.19) | −1.77 (3.52) | 7.91 (2.69) | 0.23, 7.94 | −4.50, 3.60 |
| Diastolic (mm Hg) | 9.92 (2.11) | 3.31 (1.93) | 10.27 (1.21) | −0.96, 4.11 | −3.15, 2.18 |
| Application 2 (BTDS 10) | | | | | |
| Systolic (mm Hg) | 5.00 (2.42) | −1.46 (3.38) | 6.27 (2.59) | 0.32, 8.52 | −4.21, 4.39 |
| Diastolic (mm Hg) | 4.92 (2.51) | 7.69 (1.96) | 11.09 (1.83) | −0.79, 4.78 | −3.35, 2.50 |
| Application 3 (BTDS 20) | | | | | |
| Systolic (mm Hg) | 4.27 (3.26)[d] | −2.23 (3.93) | 12.36 (3.13) | −0.60, 7.73 | −2.98, 5.75 |
| Diastolic (mm Hg) | 7.64 (2.26)[d] | 5.77 (1.92) | 11.55 (3.52) | −2.32, 2.90 | −2.52, 3.02 |
| After BTDS 20 removal | | | | | |
| Systolic (mm Hg) | 5.36 (4.88)[c] | −0.58 (3.08)[e] | 10.27 (2.22) | −5.62, 3.22 | −9.57, −0.48 |
| Diastolic (mm Hg) | 7.64 (3.08)[c] | 7.92 (2.71)[e] | 9.55 (2.16) | −3.19, 1.65 | −3.15, 1.90 |
| **Pulse rate (bpm)** | | | | | |
| Baseline | 16.67 (1.88) | 12.23 (2.14) | 12.45 (1.69) | — | — |
| Application 1 (BTDS 5) | 20.33 (2.44) | 17.38 (3.08) | 14.45 (1.64) | −0.05, 7.10 | 0.37, 7.78 |
| Application 2 (BTDS 10) | 17.50 (4.28) | 15.69 (2.37) | 15.09 (1.50) | 2.59, 9.96[c] | 1.01, 8.64[c] |
| Application 3 (BTDS 20) | 24.09 (3.58)[d] | 13.15 (2.14) | 14.27 (2.53) | 1.05, 9.67[c] | 0.35, 9.28 |
| After BTDS 20 removal | 30.82 (4.70)[d] | 13.42 (2.60)[e] | 11.64 (2.19) | 5.18, 13.24[c] | 4.38, 12.56[c] |

[a]Orthosatatic change is difference between 5-minute supine and 2-minute upright readings; mean change is the change for each subject averaged for the entire group at the specified assessment time.
[b]Assessment intervals were 6 to 8 hours following each BTDS dosing and 4 hours after BTDS removal.
[c]$P < 0.5$ for pairwise comparison (with young healthy as reference) from ANCOVA model with average orthostatic change as response variable, group as predictor variable, and baseline orthostatic change as covariate.
[d]Eleven young healthy subjects were evaluable for blood pressure and pulse rate after application 3 and BTDS 20 removal.
[e]Twelve elderly healthy subjects were evaluable for blood pressure and pulse rate after BTDS 20 removal.
[f]90% CI for adjusted least squares means analysis of adjusted to baseline orthostatic changes (ANCOVA model).

No differences in orthostatic blood pressure responses were observed between the 3 groups. The orthostatic increase in pulse was slightly, but statistically significantly larger in the young adults than in the 2 elderly groups. No syncope occurred.

Respiratory Rate and Oxygen Saturation. Table 3 summarizes data for RR and % $SaO_2$ at baseline, at 6 to 8 hours following application of each BTDS, and 4 hours after removal of BTDS 20. In all groups, changes in mean RR were small. At baseline, mean % $SaO_2$ in the 2 elderly groups w as slightly below the reference range. Compared to baseline, mean % $SaO_2$ values at each assessment did not change significantly in any of the 3 groups. No respiratory depression was observed.

TABLE 3

Changes from baseline[a] in RR and oxygen saturation (% $SaO_2$) with application of BTDS[b]

| | Mean Change (SE) | | |
|---|---|---|---|
| | Young Healthy (n = 12) | Elderly Healthy (n = 13) | Elderly Hypertensive (n = 11) |
| Respiratory rate (breaths/min) | | | |
| Baseline | 15.50 (0.96) | 13.17 (0.52) | 12.91 (0.62) |
| Change from baseline to: | | | |
| Application 1 (BTDS 5), Day 0 (8 h) | −1.00 (1.49) | 1.00 (1.19) | 0.45 (0.95) |
| Application 2 (BTDS 10), Day 3 (80 h) | −1.67 (1.10) | 1.50 (0.86) | 0.55 (1.08) |
| Application 3 (BTDS 20), Day 6 (148 h) | −2.91 (1.09)[c] | 0.83 (0.87) | 0.09 (0.64) |
| After BTDS 20 removal, Day 13 (315.5 h) | −0.55 (0.94)[c] | 0.00 (0.66)[d] | 1.27 (0.86) |

TABLE 3-continued

Changes from baseline[a] in RR and oxygen saturation (% $SaO_2$) with application of BTDS[b]

| | Mean Change (SE) | | |
|---|---|---|---|
| | Young Healthy (n = 12) | Elderly Healthy (n = 13) | Elderly Hypertensive (n = 11) |
| % $SaO_2$[e] | | | |
| Baseline | 95.42 (0.62) | 93.38 (1.32) | 93.91 (0.65) |
| Change from baseline to: | | | |
| Application 1 (BTDS 5), Day 0 (8 h) | 0.42 (0.88) | 1.00 (1.63) | −0.36 (0.59) |
| Application 2 (BTDS 10), Da 3 (80 h) | −0.17 (0.76) | 0.77 (1.14) | −0.27 (0.75) |
| Application 3 (BTDS 20), Day 6 (148 h) | −0.36 (0.92)[c] | 2.15 (1.27) | 2.00 (0.69) |
| After BTDS 20 removal, Day 13 (315.5 h) | −0.64 (0.99)[c] | 0.58 (1.54)[f] | −0.64 (1.03) |

[a]Change is from pre-BTDS (0.5 hour) to postapplication; mean change is the change for each subject averaged for the entire group at the specified assessment time.
[b]Assessment intervals were 6 to 8 hours following each BTDS application and 4 hours after BTDS removal.
[c]Eleven young healthy subjects were evaluable for RR and % $SaO_2$ after application 3 and BTDS 20 removal.
[d]Eleven elderly heathy subjects were evaluable for RR after BTDS 20 removal.
[e]Reference range: 95% to 110%.
[f]Twelve elderly healthy subjects were evaluable for % $SaO_2$ after BTDS 20 removal.

Figure 3:
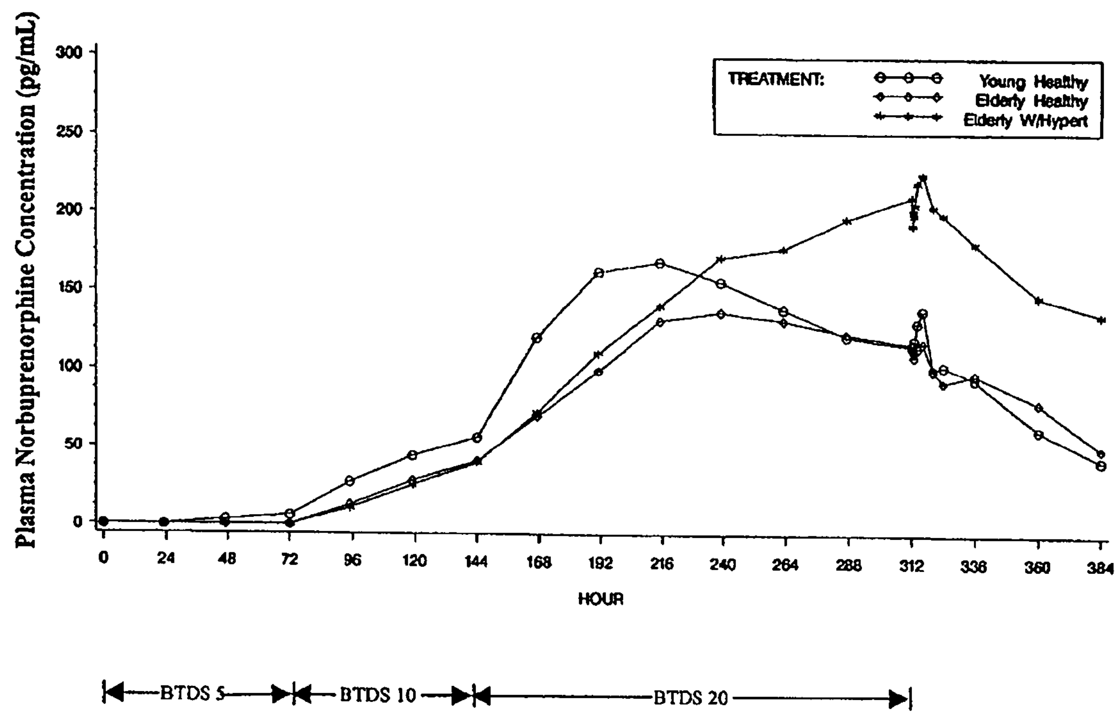
FIG. 3. Plasma concentration versus time curves for norbuprenorphine after application of BTDS 5 (0-72) hours), BTDS 10 (72-144 hours), and BTDS 20 (144-312 hours).
Figure 4:
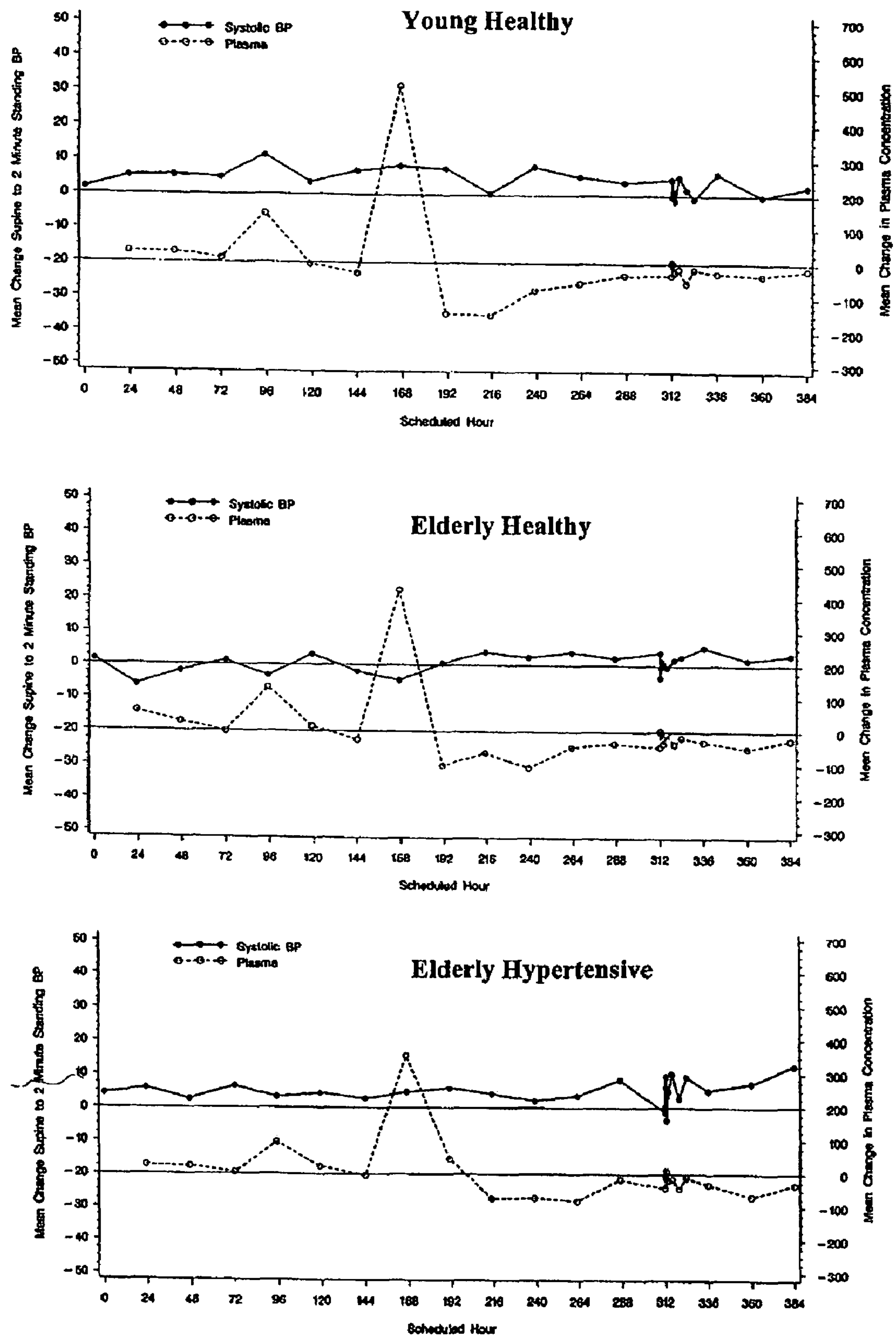
FIG. 4. Mean orthostatic change in systolic blood pressure and mean change in plasma buprenorphine concentrations, by group (N=36).
Figure 5:
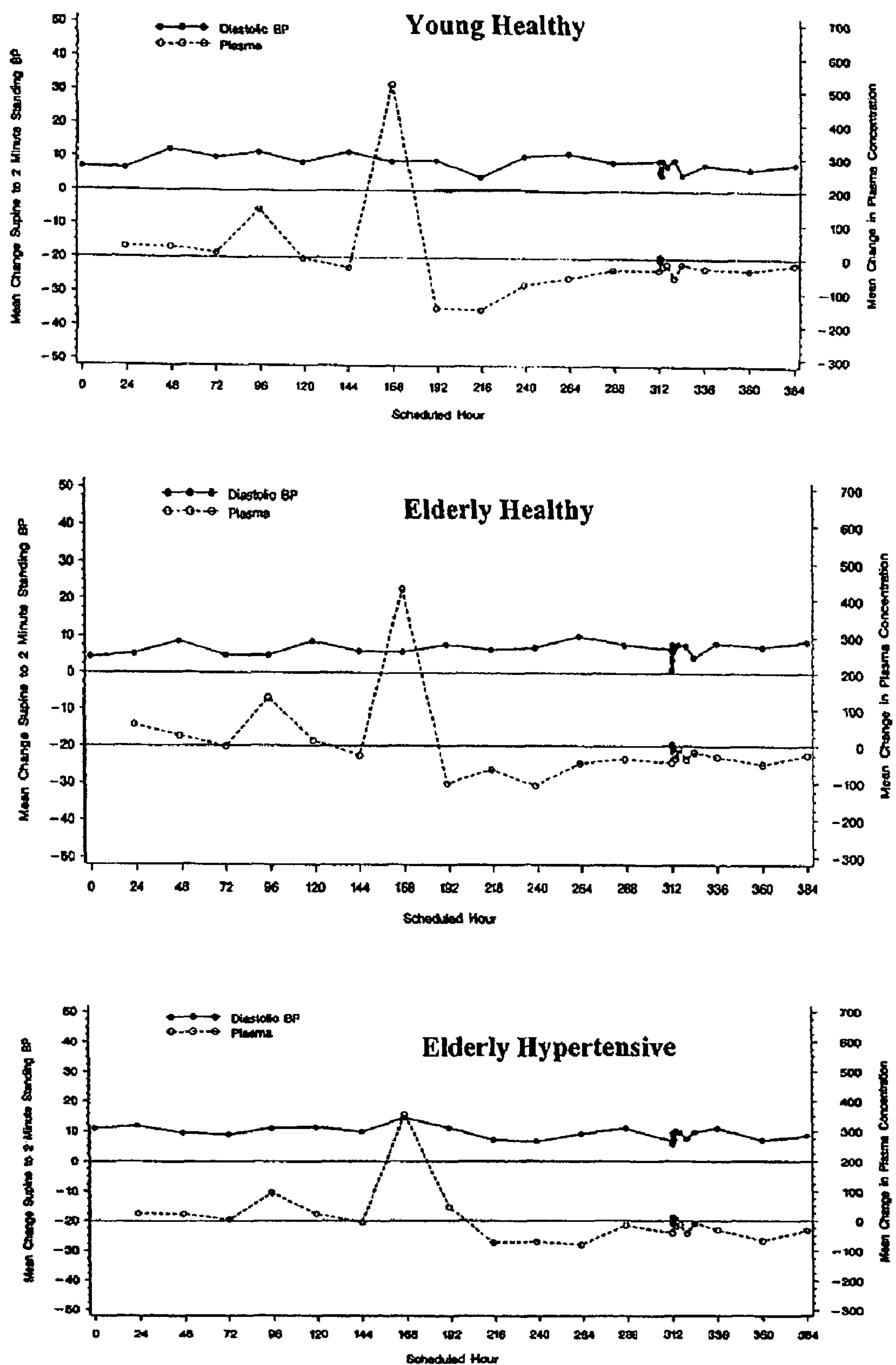
FIG. 5. Mean orthostatic change in diastolic blood pressure and mean change in plasma buprenorphine concentrations, by group (N=36).

Pharmacokinetics. Plasma concentration vs time curves for the 3 groups for buprenorphine and its metabolite, norbuprenorphine, are shown in FIGS. 2 and 3; pharmacokinetic parameters are summarized in Table 4. There were no statistically significant differences between groups for any of the buprenorphine or norbuprenorphine pharmacokinetic parameters evaluated. The $AUC_t$ and $C_{max}$ for norbuprenorphine were higher in the elderly with hypertension than in the elderly healthy or the young adult subjects.

TABLE 4

Pharmacokinetic parameters for buprenorphine and norbuprenorphine after application of BTDS 20

| | Mean (SE) | | |
|---|---|---|---|
| | Young Healthy (n = 11) | Elderly Healthy (n = 10) | Elderly Hypertensive (n = 11) |
| Buprenorphine | | | |
| $AUC_t$ (pg · h/mL) | 86026 (7808) | 78674 (7707) | 94022 (4242) |
| $AUC_\infty$ (pg · h/mL) | 87485 (8867)[a] | 81129 (8034) | 99087 (4481) |
| $C_{max}$ (pg/mL) | 722 (82) | 562 (78) | 610 (58) |
| $t_{max}$ (h) | 178 (5) | 181 (6) | 208 (13) |
| $t_{1/2}$ (h) | 29 (3)[a] | 33 (4) | 42 (2) |
| Norbuprenorphine | | | |
| $AUC_t$ (pg · h/mL) | 31359 (3447) | 26210 (3102) | 37695 (4023) |
| $AUC_\infty$ (pg · h/mL) | 33535 (3945)[a] | 30913 (3976)[b] | —[c] |
| $C_{max}$ (pg/mL) | 191 (21) | 158 (18) | 260 (40) |
| $t_{max}$ (h) | 240 (16) | 257 (14) | 295 (13) |
| $t_{1/2}$ (h) | 45 (7)[a] | 48 (5)[b] | —[c] |

[a]Ten young healthy subjects were evaluable for $AUC_\infty$ and $t_{½}$.
[b]Seven elderly healthy subjects were evaluable for $AUC_\infty$ and $t_{½}$.
[c]Four elderly subjects with hypertension were evaluable for $AUC_\infty$ and $t_{½}$ because for 7 subjects in this group, norbuprenorphine concentrations remained high at the final measurement (72 hours after removal of last BTDS).

Pharmacokinetic/Pharmacodynamic Relationship. Plotting and evaluation of mean plasma buprenorphine concentrations vs supine SBP, DBP (FIG. 4 and FIG. 5), and pulse (data not shown) indicated no relationships between plasma levels of buprenorphine and these hemodynamic parameters for any subject group.

Safety

Adverse Events. All subjects tolerated BTDS well. Adverse events reported by more than one subject in any treatment group are summarized in Table 5. Two severe, treatment-related adverse events (cholecystitis and abdominal pain, recorded for the same young adult subject) required hospitalization. Two subjects discontinued due to treatment-related adverse events: one young adult subject discontinued on study day 5 due to vomiting and one elderly healthy subject discontinued due to low blood pressure experienced on day 10. These adverse events resolved prior to discharge from the facility.

TABLE 5

Incidence of subjects with clinical adverse events reported by >1 subject in any group

| | Young Healthy (n = 12) | Elderly Healthy (n = 13) | Elderly Hypertensive (n = 11) | Total (n = 36) |
|---|---|---|---|---|
| | Subjects n (%) | | | |
| Dizziness | 8 (67) | 8 (62) | 3 (27) | 19 (53) |
| Constipation | 7 (58) | 7 (54) | 3 (27) | 17 (47) |
| Abdominal pain | 3 (25) | 6 (46) | 6 (55) | 15 (42) |
| Nausea | 6 (50) | 2 (15) | 5 (46) | 13 (36) |
| Vomiting | 4 (33) | 2 (15) | 4 (36) | 10 (28) |
| Vasodilation | 4 (33) | 1 (8) | 1 (9) | 6 (17) |
| Headache | 5 (42) | 1 (8) | 0 | 6 (17) |
| Sweating | 1 (8) | 1 (8) | 4 (36) | 6 (17) |
| Pain | 4 (33) | 0 | 1 (9) | 5 (14) |
| Pruritus at site | 2 (17) | 1 (8) | 2 (18) | 5 (14) |
| Dry mouth | 1 (8) | 1 (8) | 3 (27) | 5 (14) |
| Back pain | 3 (25) | 0 | 2 (18) | 5 (14) |
| Pruritus | 1 (8) | 1 (8) | 2 (18) | 4 (11) |
| Asthenia | 4 (33) | 0 | 0 | 4 (11) |
| Dyspepsia | 0 | 0 | 4 (36) | 4 (11) |
| Chills | 3 (25) | 0 | 1 (9) | 4 (11) |

TABLE 5-continued

| Incidence of subjects with clinical adverse events reported by >1 subject in any group | Young Healthy (n = 12) | Elderly Healthy (n = 13) | Elderly Hypertensive (n = 11) | Total (n = 36) |
|---|---|---|---|---|
| | Subjects n (%) | | | |
| Nervousness | 2 (17) | 1 (8) | 1 (9) | 4 (11) |
| Pharyngitis | 2 (17) | 2 (15) | 0 | 4 (11) |

Application Site Reactions. Application site erythema and edema for each BTDS dose are summarized in Table 6. Most of the subjects experienced mild application site reactions. None of the reports of erythema or edema were severe or dose limiting.

TABLE 6

| Application site erythema and edema at baseline and after removal of BTDS 5, 10, and 20 | Young Healthy (n = 12) | Elderly Healthy (n = 13) | Elderly Hypertensive (n = 11) |
|---|---|---|---|
| | Subjects n (%) | | |
| Erythema | | | |
| Day 0 (predose) | | | |
| No visible redness | 12 (100) | 13 (100) | 11 (100) |
| Day 3 (BTDS 5 removal) | | | |
| No visible redness | 0 | 8 (62) | 2 (18) |
| Very slight redness | 12 (100) | 4 (31) | 9 (82) |
| Slight but well-defined redness | 0 | 1 (8) | 0 |
| Moderately intense redness | 0 | 0 | 0 |
| Day 6 (BTDS 10 removal) | | | |
| No visible redness | 0 | 2 (15) | 0 |
| Very slight redness | 6 (50) | 8 (62) | 10 (91) |
| Slight but well-defined redness | 5 (42) | 3 (23) | 1 (9) |
| Moderately intense redness | 0 | 0 | 0 |
| Day 13 (BTDS 20 removal) | | | |
| No visible redness | 1 (8) | 2 (15) | 0 |
| Very slight redness | 4 (33) | 8 (62) | 6 (55) |
| Slight but well-defined redness | 7 (58) | 3 (23) | 2 (18) |
| Moderately intense redness | 0 | 0 | 3 (27) |
| Edema | | | |
| Day 0 (baseline) | | | |
| No visible reactions | 12 (100) | 13 (100) | 11 (100) |
| Very mild edema | 0 | 0 | 0 |
| Mild edema | 0 | 0 | 0 |
| Moderate edema | 0 | 0 | 0 |
| Day 3 (BTDS 5 removal) | | | |
| No visible reactions | 11 (92) | 12 (92) | 9 (82) |
| Very mild edema | 1 (8) | 1 (8) | 2 (18) |
| Mild edema | 0 | 0 | 0 |
| Moderate edema | 0 | 0 | 0 |
| Day 6 (BTDS 10 removal) | | | |
| No visible reactions | 11 (92) | 12 (92) | 6 (55) |
| Very mild edema | 0 | 1 (8) | 4 (36) |
| Mild edema | 0 | 0 | 1 (9) |
| Moderate edema | 0 | 0 | 0 |
| Day 13 (BTDS 20 removal) | | | |
| No visible reactions | 12 (100) | 13 (100) | 6 (55) |
| Very mild edema | 0 | 0 | 2 (18) |
| Mild edema | 0 | 0 | 2 (18) |
| Moderate edema | 0 | 0 | 1 (9) |

Physical Examination, Laboratory Tests, or ECG. There were no clinically significant changes in physical examination, laboratory test, or ECG results.

The effects of the disclosed dosing regimen on development of orthostatic hypotension (OH) also are shown in FIGS. 2 to 5. These figures show that transdermal administration of buprenorphine (BTDS) in escalating doses and applied repeatedly to the same application site did not result in the development of OH in young healthy subjects, elderly healthy subjects, or elderly hypertensive subjects being treated with a diuretic. In addition, none of the subjects in the trial experienced syncope (a temporary suspension of consciousness due to generalized cerebral ischaemia, a faint or swoon). The results for the subjects with hypertension also support the conclusion that concomitant use of BTDS and thiazide diuretics did not result in an increased incidence of orthostatic hypotension (OH).

The pharmacokinetic analysis further showed that there were no potentially confounding differences between the pharmacokinetics of BTDS in elderly normotensive or hypertensive subjects versus young healthy subjects. The results of this pharmacokinetic study showed that BTDS was well-tolerated. Decreased BP was observed in some of the older subjects, but none were symptomatic or considered significant. None of the younger subjects experienced decreased BP. The pharmacokinetic results demonstrate that the lack of hypotensive effect of buprenorphine via BTDS dose escalation was not due to differences in buprenorphine exposure.

Example 2

Pharmacokinetics and Safety of BTDS for 7-Day Application Comparing Healthy Elderly and Young Adult Subjects This study compares and assesses the pharmacokinetics and the effect of age on the bioavailability of a single application of a BTDS worn for 7 days.

Subject Selection

Males and non-pregnant females, aged 21-45 and greater than or equal to 65, weight range: 70 to 94 kg (males) and 55 to 81 kg (females). Patients were free of significant abnormal medical history, as evidenced by baseline physical examination, hematology, blood chemistries, urinalysis, ECG, and vital signs.

Methods

Subjects were screened during 2 weeks prior to enrollment. All subjects were dosed on the same day and all subjects received BTDS 10 (active) (10 mg (flux 10 μg/h)), BTDS 5 (placebo), and BTDS 20 (placebo) on right upper chest. Pharmacokinetic sampling was performed from predose through 7 days of application (168 hours) to 36 hours post-removal (204 hours). A total of 27 samples per subject was planned. Plasma was separated and frozen at −20° C. Blinded buprenorphine plasma concentrations were determined using the LC/MS/MS method that is validated to be linear from 25 pg/ml to 600 pg/ml. The following pharmacokinetic metrics were estimated from plasma buprenorphine and plasma norbuprenorphine concentrations following treatment with BTDS 20 (pharmacokinetic profiles were not developed for BTDS 5 or BTDS 10).

$AUC_t$ (pg·h/mL)—The area under the plasma concentration-time course profile from time=0 (system application) to the last quantifiable concentration was estimated using the linear trapezoidal rule as follows:

$$AUC_t = \sum_{L=1}^{n-1} \left[ \frac{C_{i+1} + C_i}{2} (t_1 + 1 - t_1) \right]$$

where $c_i$ is the concentration in the $i^{th}$ sample, $t_i$ is the time of the $i^{th}$ sample from dosing, and n is the number of available samples up to and including the last quantifiable concentration.

$C_{max}$ (pg/mL)—The maximum observed concentration was taken directly from the plasma concentration-time course profile.

Results

Figure 6:
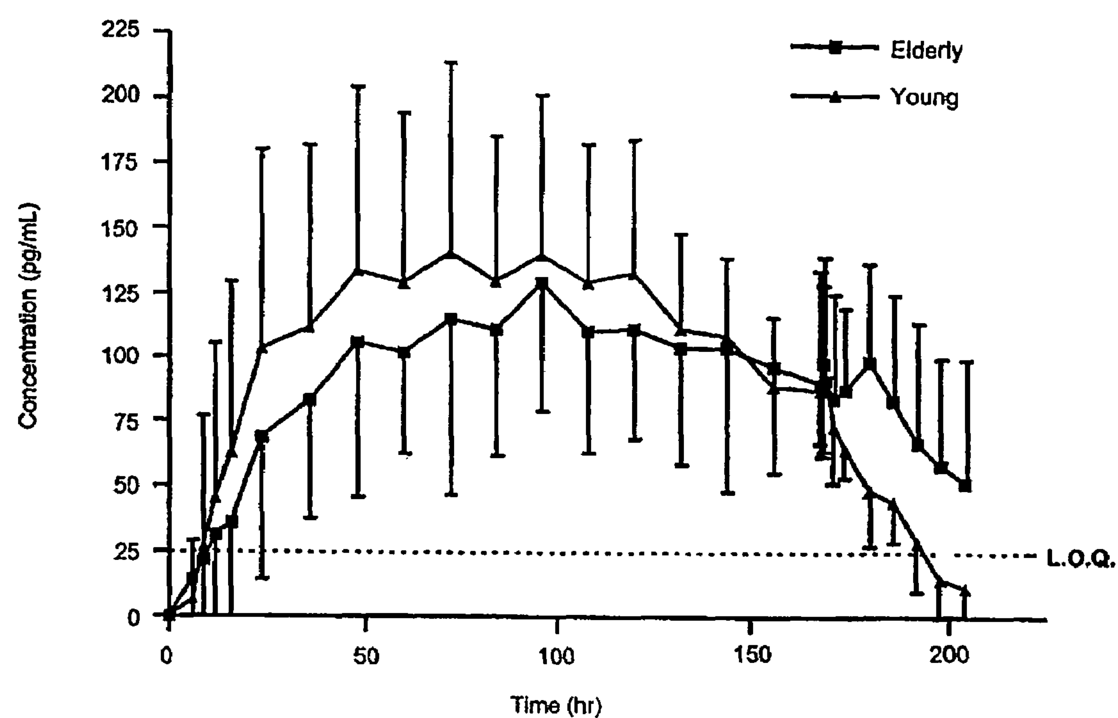
FIG. 6. Plasma buprenorphine concentrations versus time in young and elderly subjects (mean±SD).

BTDS 10, worn for 7 days, was tolerated by both elderly and young adults. Using geometric mean values to compare $AUC_t$ and $C_{max}$ in the 2 study groups, the difference between the groups was 7% for AUC, and 10% for $C_{max}$. (See FIG. 6 and Table 7). There was evidence of increased burprenorphine concentrations immediately following system removal in the elderly, although this increase did not result in adverse events. There was no treatment-limiting problems with transdermal system wear in either age group.

TABLE 7

| Mean | Elderly | Young | Elderly/Young | 90% CI |
|---|---|---|---|---|
| $AUC_t$ | 17,415 | 18,791 | 93% | 72%-120% |
| $C_{max}$ | 142 | 159 | 90% | 69%-116% |

Blood pressure studies indicated that administration of buprenorphine decreased blood pressure in both elderly and young subjects (See Table 8).

TABLE 8

| Blood pressure | Elderly | Young |
|---|---|---|
| Systolic (20 mm Hg) | 10 (83%) | 4 (33%) |
| Diastolic (10 mm Hg) | 10 (83%) | 9 (75%) |
| Systolic and Diastolic | 7 (58%) | 0 (0%) |

Mean values for body temperature, respiratory rate, and pulse were unaffected by exposure to BTDS 10. Reductions were observed in respiratory rate and/or pulse in 1 young subject and 3 elderly subjects, most commonly after removal of BTDS 10, but they were not considered significant. No respiratory rates less than 8 breaths per minute were observed. No abnormal physical examination findings emerged during BTDS 10 exposure and none of the abnormalities observed prestudy or poststudy in ECG findings were considered significant.

Figure 7:
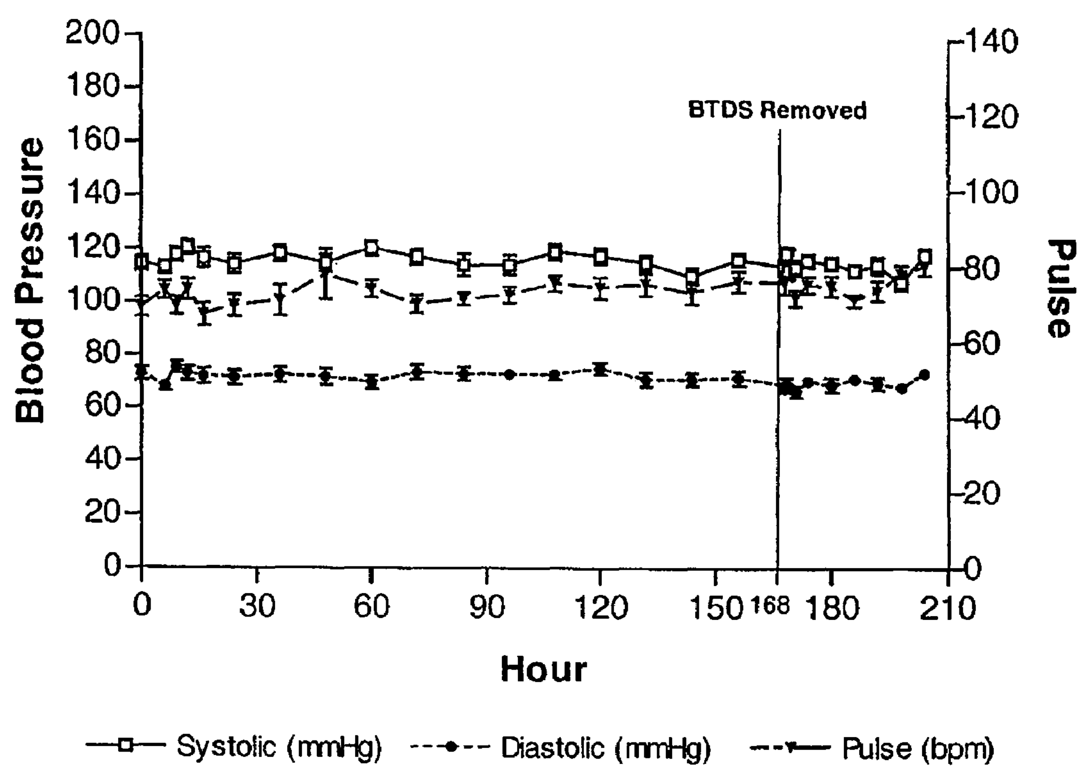
FIG. 7. Mean blood pressure and pulse rate versus time in young subjects.
Figure 8:
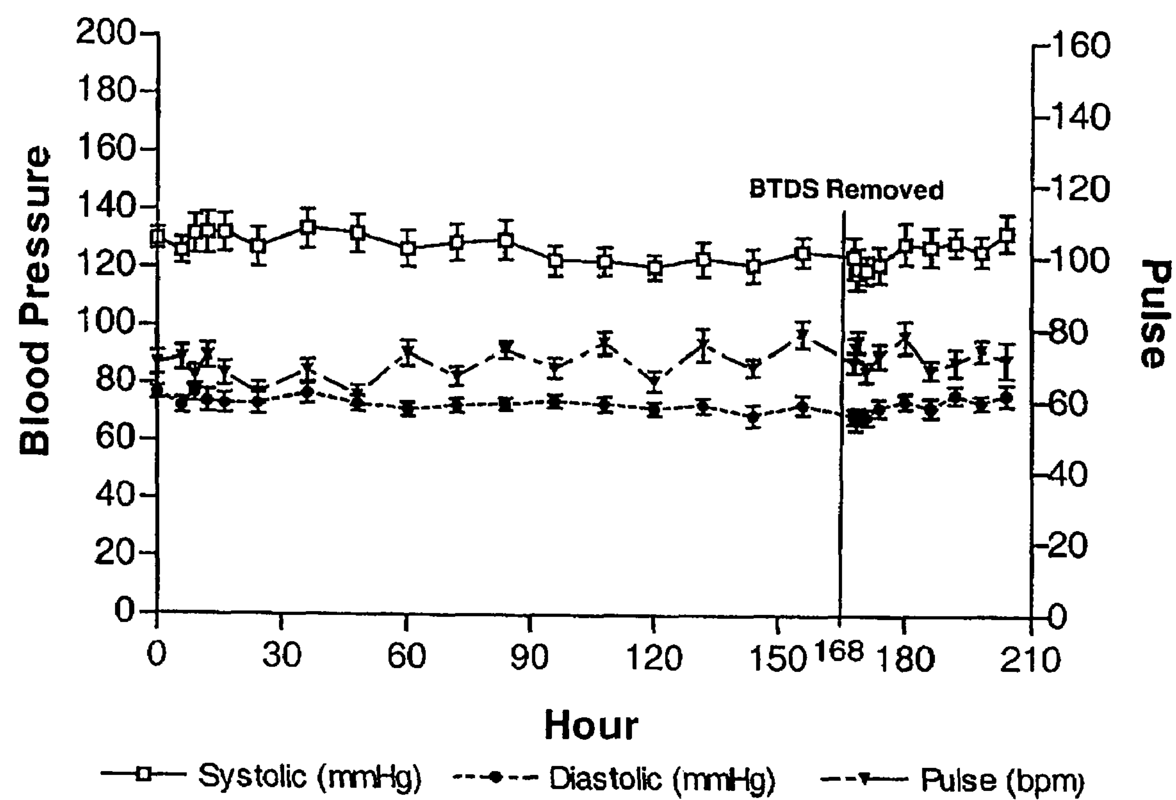
FIG. 8. Mean blood pressure and pulse rate versus time in elderly subjects.

Simultaneous declines in systolic blood pressure (SBP)≧20 mm Hg below baseline and in diastolic blood pressure (DBP)≧10 mm Hg occurred in 7 (58%) of the elderly subjects during BTDS 10 exposure. These events all resolved spontaneously. One elderly subject had mild dizziness that occurred at the same time as the blood pressure decrease. None of the young subjects experienced simultaneous decreases in SBP and DBP. (See FIGS. 7 and 8).

Adverse events by patient group are shown in Table 9.

TABLE 9

| Blood pressure | Elderly | Young |
|---|---|---|
| Constipation | 5 (42%) | 7 (58%) |
| Nausea | 5 (42%) | 6 (50%) |
| Vomiting | 3 (25%) | 6 (50%) |
| Headache | 2 (17%) | 6 (50%) |
| Dizziness | 3 (25%) | 2 (17%) |
| Somnolence | 2 (17%) | 2 (17%) |

Buprenorphine via other routes has shown effects on blood pressure similar to those seen in this study. Catheline et al., (1980) showed similar dose response curves for intramuscular buprenorphine and intramuscular morphine on blood pressure, pulse, and ventilation, while Heel et al. (Drugs 1979; 17:81-110) reported a decrease of approximately 10% in systolic blood pressure as well as a slight decrease in diastolic blood pressure following oral buprenorphine. The present study's findings of a decrease in blood pressure also confirms previous work by Melon et al., Anesth Anal Rean 1980, 37:121-125 showing decrease in mean arterial pressure of approximately 10 mm Hg and decrease in heart rate of approximately 10 pbm following parenteral buprenorphine.

Another opioid, fentanyl, is currently available in a transdermal formulation, but it is associated with altered pharmacokinetics in the elderly (Holdsworth et al., Gerontology 1994, 40:32-37; Bentley et al., Anesth Analg 1982, 61:968-971; Thompson et al., Br J Anaesth 1998, 81:152-154). In a study of IV fentanyl pharmacokinetics and age, it was found that comparable doses of IV fentanyl result in higher serum drug concentrations in the elderly due to prolonged elimination resulting from decreased drug clearance in this population (Bentley, 1982). Evaluations of comparative pharmacokinetic performance of 2 transdermal formulations of fentanyl have been published (Holdsworth et al., Gerontology 1994, 40:32-37; Thompson et al., Br J Anaesth 1998, 81:152-154). In a study of a 24 hour fentanyl transdermal system, there was a trend for elderly subject to achieve a greater $C_{max}$ than young adult subjects (Holdsworth et al., Gerontology 1994, 40:32-37). Because 10 elderly subjects had the patch removed prematurely due to adverse events, AUC was divided by duration of patch wear in order to compare the elderly and young adult subjects. When AUC was corrected for actual duration of patch wear, the elderly subjects had significantly greater average exposure to fentanyl than did the young did the young adults. This study showed that this 24 hour fentanyl transdermal system could not provide pharmacokinetically interchangeable performance in the elderly relative to young adults.

For a different 3 day fentanyl transdermal system in elderly subjects, 2 of 9 elderly subjects had fentanyl transdermal systems removed before the end of study due to respiratory depression (less than 8 breaths/minute) (Thompson et al., Br J Anaesth 1998, 81:152-154). The increase in plasma fentanyl concentrations was significantly slower in the elderly than in the young adult subjects (mean half-time, 11.1 hours versus 4.2 hours, respectively, with P=0.005). Therefore, the studies described above show that 2 different fentanyl transdermal systems did not provide pharmacokinetically interchangeable performance in the elderly relative to young adults. Thus, experience with these 2 fentanyl transdermal systems demonstrates that providing transdermal pharmacokinetic performance in the elderly comparable to that seen in young adults represents a technical challenge.

Notably, drug-induced orthostatic hypotension is a major cause of morbidity in the elderly (Verhaeverbekel, Drug Sat., 1997, 17:105-108). Falls resulting from orthostatic hypotension and other syncopal episodes account for 40% of nursing home admissions and considerable medical problems in this age group. The elderly hypertensive are at particular risk because of iatrogenic hypovolemia resulting in decreased cardiac preload and decreased autonomic function (e.g., adrenergic receptor responsiveness and baroreflexes).

This study showed that BTDS 10 provided consistent buprenorphine blood concentrations in both elderly and young adults.

Example 3

Analgesic Efficacy and Safety Buprenorphine Transdermal System (BTDS) in Patients with Osteoarthritis This Example is designed to evaluate the analgesic efficacy and safety of an escalating dose transdermal system containing buprenorphine, a partial mu-opioid agonist, compared with placebo in patients with osteoarthritis who could not achieve adequate pain control with ibuprofen alone.

Methods

The study design entails screening patients taking opioids for control of chronic pain associated with osteoarthritis. Opioid medications are stopped when pain levels are less than 7 on the pain scale, and ibuprofen 1600 mg/day is administered as an open-label run-in for 7 days. After 7 days of ibuprofen, if pain levels are greater than or equal to 7, randomization to double-blind titration is carried out to administer placebo or BTDS (5-10-20 mcg/h) every 3 days. After 7 days, the maintenance dosage is the final BTDS dosage administered at least every 3 days as long as the target analgesia level is achieved. (If pain control is not achieved, one or more subsequent BTDS dosage levels may be administered, titrating up to 40 mg.) After 21 days, double-blind maintenance is followed for 7 days.

The primary efficacy variable is the percentage of patients treated successfully for pain analyzed at the end of the maintenance period (day 28). Treatment is considered successful if patients does not discontinue early due to lack of efficacy (DOLE) and if their score for patient satisfaction with medication for pain (patient satisfaction) ("how would you rate the study medication you received for pain?") at the final visit is 2, 3, or 4, where 0 is poor, 1 is fair, 2 is good, 3 is very good, and 4 is excellent. The secondary efficacy variables include average pain intensity over the last twenty-four hours, patient satisfaction, and dose level at the end of the titration period. The percentage of patients treated successfully for pain is analyzed using logistic regression, with terms for treatment and center and other appropriate covariates. For average pain intensity and patient satisfaction, a linear mixed model with terms for treatment and center and other appropriate covariates is used. Cochran-Mantel-Haenszel chi-square analysis is performed for the dose level at the end of the titration period.

Example 4

The Effectiveness and Safety of BTDS Compared with Hydrocodone/Acetaminophen in the Treatment of Patients with Chronic Lower Back Pain This Example is designed to compare the effectiveness of BTDS, a matrix transdermal system containing buprenorphine, to hydrocodone/acetaminophen (HCD/APAP) tablets in patients with chronic lower back pain.

Methods

During a 7-day run-in period, patients discontinue all analgesics and take 400 mg ibuprofen qid, which they continue throughout the study. During the first 7 days, patients titrate to an effective level of analgesia (3 dosage levels: BTDS 5, 10, 20 mcg/h); applied every 3 days, or HCD/APA (2.5 mg hydrocodone/250 mg acetaminophen; 1, 2, or 3 tablets qid). Patients continue on an acceptable effective dose for a predetermined maintenance period.

Primary efficacy variables are Average Pain Intensity over the Last 24 hours (0-10 scale) and Patient Satisfaction with Medication for Pain (0-4 scale) for the maintenance period. Repeated measures linear mixed model with terms for treatment and center and other appropriate covariates are used. Least squares means (LS means), SE and 95% CI are estimated. Equivalence is demonstrated if the 95% CI was contained within (−2,2) for average pain intensity and within (−1,1) for patient satisfaction. An effect size (ES) meta-analysis for published hydrocodone versus placebo studies (7) is performed. The ES is calculated for each study (ES is the mean difference (hydrocodoen−placebo)/SD). A DerSimonian pooled ES and 95% CI are calculated, allowing for an indirect test of the null hypothesis for BTDS.

Example 5

A Comparative Efficacy Study of Buprenorphine TDS, Oxycodone/Acetaminophen and Placebo in Patients with Chronic Back Pain The present example evaluates the analgesic efficacy of buprenorphine transdermal system (BTDS).

Methods

This was a placebo and active controlled, multiple dose, double-blind, parallel group multicenter, safety and efficacy study. Patients were randomized to 1 of 3 treatment groups. Patents were allowed to titrate to 1 of 3 dose levels for effectiveness during the first 21 days of the study. Patients continued their stable dose of NSAIDS throughout the duration of the study. 54 males and 80 females with a mean age of 52 years (range 19-85 years) participated in the study. 80% were opioid naïve and 20% were opioid experienced. The efficacy primary variable was measured as pain on average and pain at the present moment. The secondary efficacy variable was discontinuation due to lack of efficacy, medical outcomes study health survey, therapeutic response, patient preference, daily patient diary for average pain, time to stable pain management, and number of post-titration dose adjustments. Statistical methods included repeated measures analysis for pain items and pairwise contrasts for comparisons of interest, 90% confidence intervals for Medical Outcome Study health survey items. Cox proportional hazards regression analysis for time to discontinuation due to lack of efficacy and for time to stable pain management.

Results

Efficacy differences in the least squares mean change from baseline for "pain on average" between the BTDS and the placebo groups were statistically significant for the maintenance period, Days 21 and 30 (P=0.009) (FIG. 9). Differences in the least squares mean change from baseline for "pain right now" between the BTDS and the placebo groups were statistically significant for the maintenance period as determined by days 21 and 30 (P=0.028) (FIG. 10). Results of the secondary efficacy analyses support the efficacy observed in the analysis of the primary variables. Discontinuations due to lack of efficacy were greater in the placebo group than in the Oxy/APAP and the BTDS groups. The percentage of patients discontinuing due to lack of efficacy at the end of the study was 44% in the placebo 16% in the BTDS group, and 2% in the Oxy/APAP groups. (FIG. 11). Cox proportional hazards regression analysis, comparing rates of discontinuation, showed hazard rations of 0.30 with BTDS compared with placebo, which was statistically significant (P=0.01). Cox proportional hazards regression analysis, comparing time to stable pain management, showed hazard ratios of 1.67 for BTDS and 1.51 for oxy/APAP group compared to placebo. Statistical analysis of rations between BTDS and placebo resulted in P=0.054. Patient satisfaction with study medication showed greater satisfaction with Oxy/APAP and BTDS than with placebo.

Discussion

The efficacy of BTDS for the treatment of chronic back pain was demonstrated in this study. Difference in the lease squares mean change from baseline were statistically significant, by repeated measures analysis, for the maintenance period of the study, for both the primary efficacy variables "pain on average" and "pain right now" for the BTDS group compared with placebo. The positive findings from the primary analyses were supported by the results for the secondary variables, including Cox proportional hazards regression analysis, comparing rates of discontinuation due to lack of efficacy, which showed a statistically significant differences between the BTDS and the placebo groups. The addition of BTDS to the treatment plan of selected patients who had not achieved adequate pain control with NSAIDS alone resulted in significant improvement relative to placebo.

Example 6

A Comparative Study of the Incidence of Adverse Effects as a Function of Dose Escalation Regimen The present example compares the relative incidence of adverse events in healthy subjects receiving BTDS 20 with (Group 1) or without (Group 2) prior dose escalation.

Methods

Group 1. The selection criteria and study design for the subjects in Group 1 were identical to those described in Example 1, combining elderly hypertensive, elderly healthy, and young healthy subjects. Briefly, elderly hypertensive subjects were hypertensive males or females, aged 65-80 years, body weight ranging from 70-94 kg (males) and 55 to 81 kg (females); elderly healthy subjects were males or females aged 65-74 years, inclusive, body weight ranging from 70-94 kg (males) and 55 to 81 kg (females), and young healthy subjects were males or females aged 21-40 years, body weight ranging from 70-94 kg (males) and 55 to 81 kg (females). The total number of subjects in Group 1 was 36.

All subjects in Group 1 were administered BTDS 5 from day 0 to day 3, BTDS 10 from day 3 to day 6, and BTDS 20 from day 6 to day 13. After day 13, patients were monitored for an additional 4 days (day 17). Any adverse events reported by more than one patient during the period day 0 to day 17 were noted and used for statistical analysis according to the methods described in Example 1.

Group 2. The selection criteria for the subjects in Group 2 were as follows: healthy adult subjects, aged 18 to 80 years, inclusive (mean age 35), body weight ranging from 42 to 107 kg (mean weight 74 kg), 34% of the subjects being female. The total number of subjects in Group 2 was 78.

All subjects in Group 2 were administered BTDS 20 from day 0 to day 7. After day 7, patients were monitored for an additional 3 days. Any adverse events reported by more than one patient during the period day 0 to day 10 were noted and used for descriptive analysis according to the methods described in Example 1.

Results

The incidence of adverse events noted for the subjects in Groups 1 and 2 are shown in Table 10. As shown in Table 10, subjects which were titrated to BTDS 20 displayed an overall lower incidence of adverse events. Although a higher number of subjects in Group 1 reported constipation, the incidence of headache, nausea and vomiting was notably decreased by dose escalation to BTDS 20 rather than applying BTDS 20 directly.

TABLE 10

Adverse Events in Healthy Subjects - Effect of Escalation Schedule

| Adverse Event | Group 1 (n = 36) (dose escalation) | Group 2 (n = 78) (no dose escalation) |
|---|---|---|
| Headache | 17% | 37% |
| Dizziness | 53% | 55% |
| Nausea | 36% | 52% |
| Vomiting | 28% | 38% |
| Constipation | 47% | 33% |
| Rash (site) | 2% | 7% |
| Pruritis (site) | 14% | 14% |
| Urinary retention | — | 8% |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, publications, procedures, and the like are cited throughout this application and in the Bibliography, the disclosures of which are incorporated herein by reference in their entireties.

What is claimed is:

1. A method of treating chronic pain in a patient in need of such treatment, which method comprises:

administering to the patient a first buprenorphine-containing transdermal dosage form for a first dosing period that is no longer than 5 days;

administering to the patient a second buprenorphine-containing transdermal dosage form for a second dosing period that is no longer than 5 days, wherein the second dosage form comprises the same dosage of buprenorphine as, or a greater dosage of buprenorphine than, the first dosage form; and administering to the patient a third buprenorphine-containing transdermal dosage form for a third dosing period, wherein the third dosage form comprises a greater dosage of buprenorphine than the second dosage form.

2. The method of claim 1, wherein the first, second, and third transdermal dosage forms contain the amounts of buprenorphine as set forth in a row of the following table:

| First (mg) | Second (mg) | Third (mg) |
|---|---|---|
| 5 | 5 | 10 |
| 5 | 5 | 20 |
| 5 | 5 | 30 |
| 5 | 10 | 20 |
| 5 | 10 | 30 |
| 5 | 10 | 40 |
| 5 | 20 | 40 |
| 5 | 30 | 40 |
| 10 | 10 | 20 |
| 10 | 10 | 30 |
| 10 | 10 | 40 |
| 10 | 20 | 30 |
| 10 | 20 | 40 |
| 10 | 30 | 40 |
| 20 | 20 | 30 |
| 20 | 30 | 40. |

3. The method of claim 1, wherein the first dosing period is at least 2 days.

4. The method of claim 1, wherein the second dosing period is at least 2 days.

5. The method of claim 1 wherein the third dosing period is at least 2 days.

6. The method of claim 1, wherein the first dosing period is no longer than 4 days.

7. The method of claim 1, wherein the first dosing period is 3 days.

8. The method of claim 1, wherein the second dosage period is no longer than 4 days.

9. The method of claim 1, wherein the second dosage period is 3 days.

10. The method of claim 1 wherein the first dosage form comprises 5 mg of buprenorphine.

11. The method of claim 1 wherein the second dosage form comprises 10 mg of buprenorphine.

12. The method of claim 1 wherein the third dosage form comprises 20 mg of buprenorphine.

13. The method of claim 1, wherein the third dosage form comprises 30 mg of buprenorphine.

14. The method of claim 1, wherein the third dosage form comprises 40 mg of buprenorphine.

15. The method of claim 1, further comprising administering a fourth buprenorphine-containing transdermal dosage form for a fourth dosing period at least once after the third dosing period.

16. The method of claim 15, wherein the fourth dosing period is 2 days.

17. The method of claim 15, wherein the fourth dosage form comprises 30 or 40 mg of buprenorphine.

18. The method of claim 1 wherein the patient is an elderly patient.

19. The method of claim 18 wherein the patient is an elderly hypertensive patient.

20. The method of claim 1 wherein the patient is a pediatric patient.

21. The method of claim 20 wherein the pediatric patient suffers from a condition selected from the group consisting of scoliosis, cerebral palsy, juvenile arthritis, cancer and postoperative pain.

22. The method of claim 1 wherein the chronic pain is pain expected to last for at least one week.

23. The method of claim 22, wherein the patient is suffering from at least one of osteoarthritis, chronic lower back pain, postoperative pain, or pain associated with recovery from extensive trauma.

24. The method of claim 1, wherein the first dosage form comprises up to 5 mg of buprenorphine, the first dosing period is up to 3 days, the second dosage form comprises up to 5 mg of buprenorphine, the second dosing period is up to 3 days; the third dosage form comprises up to 20 mg of buprenorphine, and the third dosing period at least about 7 days.

25. The method of claim 1, wherein the transdermal dosage form is selected from the group consisting of a topical gel, a lotion, an ointment, and an iontophoretic delivery system.

26. The method of claim 1, wherein the method decreases the systolic blood pressure of the patient by at least 20 mmg, or the diastolic blood pressure by at least 10 mmHg.

27. The method of claim 1, wherein the method decreases the systolic blood pressure of the patient by at least 20 mmHg, and the diastolic blood pressure by at least 10 mmHg.

28. A method of treating chronic pain in a patient in need of such treatment, which method comprises administering to the patient a first, a second, and a third transdermal dosage form of buprenorphine, wherein the third dosage form comprises a higher dosage of buprenorphine than the first and second dosage forms, and wherein the method does not increase the incidence of an adverse event selected from nausea, vomiting, and headache as compared to only administering the same dosage of buprenorphine as the third dosage form.

29. The method of claim 28 wherein the method does not induce orthostatic hypertension or syncope.

30. The method of claim 28, wherein the first dosage form comprises no more than 5 mg, the second dosage form comprises no more than 10 mg buprenorphine and is administered for a dosing period of three days, and the third dosage form comprises at least 20 mg buprenorphine and is administered for a dosing period of at least 2 days.

31. The method of claim 28, wherein the first dosage form comprises no more than 10 mg buprenorphine, the second dosage form comprises no more than 20 mg buprenorphine and is administered for three days, and the third dosage form comprises at least 30 mg buprenorphine and is administered for at least 2 days.

32. The method of claim 28, wherein the first dosage form comprises no more than 20 mg buprenorphine, the second dosage form comprises no more than 30 mg buprenorphine and is administered for three days, and the third dosage form comprises 40 mg buprenorphine and is administered for at least 2 days.

33. The method of claim 27, wherein the patient is an elderly patient.

34. The method of claim 33, wherein the patient is an elderly hypertensive patient.

35. The method of claim 34, wherein the patient is taking thiazide diuretics for treatment of hypertension.

36. The method of claim 34, wherein the method decreases the systolic blood pressure of the patient by at least 20 mmHg, or the diastolic blood pressure by at least 10 mmHg.

37. The method of claim 34, wherein the method decreases the systolic blood pressure of the patient by at least 20 mmHg, and the diastolic blood pressure by at least 10 mmHg.

38. A method of treating chronic pain in a patient in need of such treatment, which method comprises:

administering to the patient a first buprenorphine-containing transdermal dosage form for a first dosing period that is no more than 5 days;

administering to the patient a second buprenorphine-containing transdermal dosage form for a second dosing period, wherein the second dosage form comprises the same dosage of buprenorphine as, or a greater dosage of buprenorphine than, the first dosage form; and administering to the patient a third buprenorphine-containing transdermal dosage form for a third dosing period, wherein the third dosage form comprises a greater dosage of buprenorphine than the second dosage form, wherein the dosing regimen results in a plasma buprenorphine profile wherein a) the mean plasma buprenorphine concentration 24 hours after administration of the first dosage form is between 10-100 pg/ml;

b) the mean plasma buprenorphine concentration 72 hours after administration of the first dosage form is between 25-200 pg/ml;

c) the mean plasma buprenorphine concentration 144 hours after administration of the first dosage form is between 100-250 pg/ml; and d) the mean plasma buprenorphine concentration 168 hours after administration of the first dosage form is between 400-1000 pg/ml.

39. The method of claim 38, wherein a) the mean plasma buprenorphine concentration 24 hours after administration is between 20-50 pg/ml;

b) the mean plasma buprenorphine concentration 72 hours after administration is between 40-100 pg/ml;

c) the mean plasma buprenorphine concentration 144 hours after administration is between 150-200 pg/ml; and d) the mean plasma buprenorphine concentration 168 hours after administration is at least 500 pg/ml.

40. The method of claim 38 wherein the patient is elderly.

41. The method of claim 40 wherein the patient has hypertension.

42. The method of claim 38, wherein the transdermal dosage form is selected from the group consisting of transdermal dosage article and transdermal dosage composition.

43. The method of claim 42, wherein the transdermal dosage article is a diffusion-driven transdermal system.

44. The method of claim 42, wherein the transdermal dosage composition is selected from the group consisting of a topical gel, a lotion, an ointment, and an iontophoretic delivery system.

45. A method of treating chronic pain in a patient in need of such treatment, which method comprises:

administering to the patient a first buprenorphine-containing transmucosal dosage form for a first dosing period that is no more than 5 days;

administering to the patient a second buprenorphine-containing transmucosal dosage form for a second dosing period, wherein the second dosage form comprises the same dosage of buprenorphine as, or a greater dosage of buprenorphine than, the first dosage form; and administering to the patient a third buprenorphine-containing transmucosal dosage form for a third dosing period, wherein the third dosage form comprises a greater dosage of buprenorphine than the second dosage form, wherein the dosing regimen results in a plasma buprenorphine profile wherein a) the mean plasma buprenorphine concentration 24 hours after administration of the first dosage form is between 10-100 pg/ml;

b) the mean plasma buprenorphine concentration 72 hours after administration of the first dosage form is between 25-200 pg/ml;

c) the mean plasma buprenorphine concentration 144 hours after administration of the first dosage form is between 100-250 pg/ml; and d) the mean plasma buprenorphine concentration 168 hours after administration of the first dosage form is between 400-1000 pg/ml.

46. The method of claim 45, wherein the transmucosal dosage form is selected from the group consisting of a transmucosal dosage article and a transmucosal dosage composition.

47. The method of claim 46, wherein the transdermal dosage composition is selected from the group consisting of a transmucosal system, and a transmucosal device.

* * * * *